US010174008B2

(12) United States Patent
Tang et al.

(10) Patent No.: US 10,174,008 B2
(45) Date of Patent: Jan. 8, 2019

(54) SYNTHESIS OF CYCLOPROPYL INDOLES AND CYCLOHEPTA[B]INDOLES, PHARMACEUTICAL COMPOSITIONS CONTAINING THEM AND METHOD OF USING THEM

(71) Applicant: WISCONSIN ALUMNI RESEARCH FOUNDATION, Madison, WI (US)

(72) Inventors: Weiping Tang, Middleton, WI (US); Xiaoxun Li, Mountain View, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 26 days.

(21) Appl. No.: 15/545,858

(22) PCT Filed: Dec. 3, 2015

(86) PCT No.: PCT/US2015/063648
§ 371 (c)(1),
(2) Date: Jul. 24, 2017

(87) PCT Pub. No.: WO2016/090094
PCT Pub. Date: Jun. 9, 2016

(65) Prior Publication Data
US 2018/0002318 A1 Jan. 4, 2018

Related U.S. Application Data

(60) Provisional application No. 62/086,762, filed on Dec. 3, 2014.

(51) Int. Cl.
B01J 31/22 (2006.01)
B01J 31/40 (2006.01)
C07B 37/10 (2006.01)
C07B 51/00 (2006.01)
C07D 209/08 (2006.01)
C07D 405/08 (2006.01)

(52) U.S. Cl.
CPC ........ C07D 405/08 (2013.01); B01J 31/2265 (2013.01); B01J 31/4046 (2013.01); C07B 37/10 (2013.01); C07B 51/00 (2013.01); C07D 209/08 (2013.01); B01J 2231/325 (2013.01); Y02P 20/55 (2015.11)

(58) Field of Classification Search
CPC .... C07D 405/08; C07D 209/08; C07B 51/00; C07B 37/10; B01J 31/2265; B01J 31/4046; B01J 2231/325
See application file for complete search history.

(56) References Cited

FOREIGN PATENT DOCUMENTS

WO WO 2007/047775 A1 4/2007

OTHER PUBLICATIONS

Trost et al. "Rhodium-Catalyzed Cycloisomerization: Formation of Indoles, Benzofurans, and Enol Lactones" Angew. Chem. Int. Ed. 2007, 46, 2074-2077. (Year: 2007).*
Ye et al. "Gold-catalyzed intramolecular hydroamination of terminal alkynes in aqueous media: efficient and regioselective synthesis of indole-1-carboxamides" Green Chem. 2009, 11, 1201-1208. (Year: 2009).*
Zhang et al. "One pot hydroamination/[4 + 3] cycloaddition: synthesis towards the cyclohepta[b]indole core of silicine and ervatamine" RSC Adv. 2014, 4, 63850-63854. (Year: 2014).*
Kumar et al. "Discovery and optimization of a new class of pyruvate kinase inhibitors as potential therapeutics for the treatment of methicillin-resistant Staphylococcus aureus infections" Bioorg. Med. Chem. 2014, 22, 1708-1725. (Year: 2014).*
Elango et al. "Novel Aza and Oxa Wittig-Horner Reactions of Dietyl (1-Benzenesulfonyl)indol-2-yl Methyl Phosphonate" Synth. Commun. 1999, 29, 2043-2051. (Year: 1999).*
Gritsch et al. "Enantioselective Synthesis of Cyclohepta[b]indoles: Gram-Scale Synthesis of (S)-SIRT1-Inhibitor IV" Org. Lett. 2013, 15, 5472-5475. (Year: 2013).*
Joule, J. A. "Product Class 13: Indole and Its Derivatives" Science of Synthesis 2001, 10, 361-652. (Year: 2001).*
U.S. Appl. No. 12/473,605, Bursavich et al., filed Dec. 17, 2009.
U.S. Appl. No. 10/713,893, Mattson, filed Nov. 23, 2004.
Wang et al., Combining Zn Ion Catalysis with Homogeneous Gold Catalysis: An Efficient Annulation Approach to N-Protected Indoles; Chem Sci. Feb. 1, 2013; 4(2): doi:10.1039/C2SC21333H.
Nomura et al., Novel Indole-N-Glucoside, TA-1887 As a Sodium Glucose Cotransporter 2 Inhibitor for Treatmeant of Type 2 Diabetes, ACS Med. Chem. Lett. 2014, vol. 5, pp. 51-55.

* cited by examiner

Primary Examiner — Amanda L Aguirre
(74) Attorney, Agent, or Firm — Joseph T. Leone, Esq.; DeWitt Ross & Stevens S.C.

(57) ABSTRACT

Methods of making indole analogs using a rhodium-containing catalyst are described, along with methods of using the compounds to treat hyperglycemic, hyperlipidemic, or autoimmune disorders in mammals, and corresponding pharmaceutical compositions. Disclosed herein is a method of making indoles. The method comprises contacting a reactant of formula I wherein E is a protecting group, —SO2-Aryl, or —SO2-substituted-Aryl; and R and R2 are independently selected from the group consisting of hydrogen, halo, C1-C12-alkyl and aryl; with a rhodium(1)-containing catalyst.

20 Claims, No Drawings

SYNTHESIS OF CYCLOPROPYL INDOLES AND CYCLOHEPTA[B]INDOLES, PHARMACEUTICAL COMPOSITIONS CONTAINING THEM AND METHOD OF USING THEM

FEDERAL FUNDING STATEMENT

This invention was made with government support under GM088285 awarded by the National Institutes of Health. The government has certain rights in the invention.

BACKGROUND

Metal carbenes are versatile intermediates for a variety of reactions.[1] Conventionally, they are generally derived from diazo compounds or related derivatives.[2] However, some metal carbenes cannot be generated from diazo compounds easily, such as Rh(I)-carbenes.[3] Fisher carbenes have been the primary precursors of Rh(I)-carbenes for cycloadditions.[4] Several groups have discovered that Rh(I)-carbenes can be derived from 1,2-acyloxy migration of propargylic esters for cycloadditions.[5,6,7] It has also recently been found that ynamides and 3-hydroxy-1,4-enynes can serve as Rh(I)-carbene precursors in cycloaddition and cycloisomerization reactions.[8] Despite much progress, however, there remains a long-felt and unmet need for versatile carbene intermediates to make indoles.

SUMMARY OF THE INVENTION

Disclosed herein is a method of making indoles. The method comprises contacting a reactant of formula I:

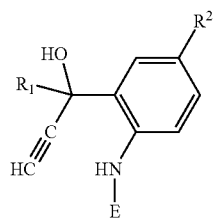
(I)

wherein E is a protecting group, —SO$_2$-Aryl, or —SO$_2$-substituted-Aryl; and R$^1$ and R$^2$ are independently selected from the group consisting of hydrogen, halo, C$_1$-C$_{12}$-alkyl, and aryl; with a rhodium(I)-containing catalyst. The catalytic reaction can take place in the presence of or in the absence of an alkene-containing co-reactant. The reaction is conducted for a time and at a temperature to yield a product mixture comprising formula (II), (III), and/or (IV):

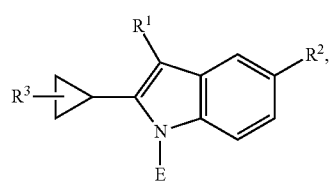
(II)

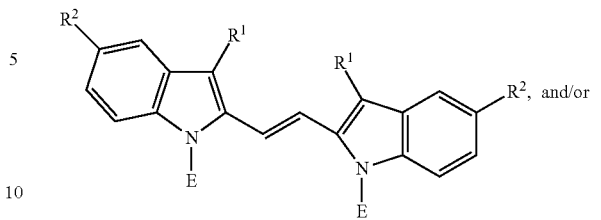
(III)

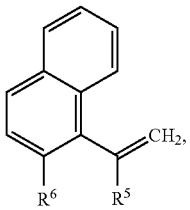
(IV)

wherein R$^1$, R$^2$, and E are as defined previously, and R$^3$ is hydrogen in the absence of the alkene-containing co-reactant, and R$^3$ is a substituent corresponding to the alkene-containing co-reactant in the presence of the alkene-containing co-reactant.

The rhodium(I)-containing catalyst may optionally comprise [Rh(CO)$_2$Cl]$_2$.

In some versions, the reaction is conducted in the presence of carbon monoxide.

If an alkene-containing co-reactant is used, it may optionally be selected from the group consisting of:

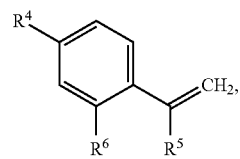

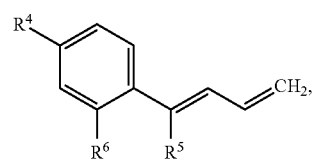

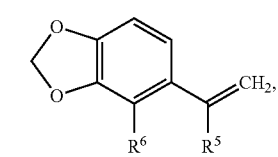

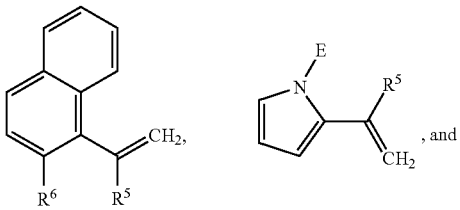
, and

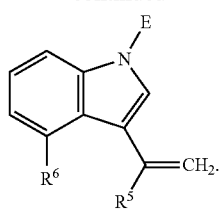

wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; and E is a protecting group.

Also disclosed herein is a method of treating hyperglycemic, hyperlipidemic, or autoimmune disorders in mammals. The method comprises administering to a mammal an anti-hyperglycemic-effective, anti-hyperlipidemic, or anti-autoimmune amount of one or more the indole analogs selected from the group consisting of:

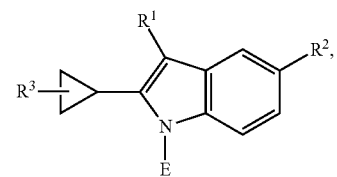
(II)

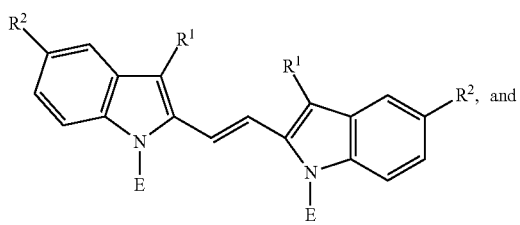
(III)

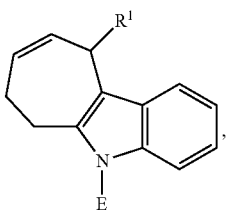
(IV)

wherein $R^1$ and $R^2$ are independently selected from the group consisting of hydrogen, halo, $C_1$-$C_{12}$-alkyl, and aryl; and $R^3$ is selected from the group consisting of:

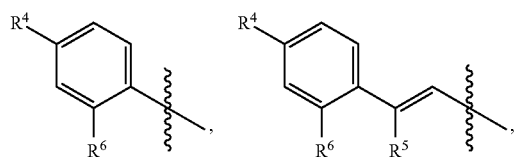

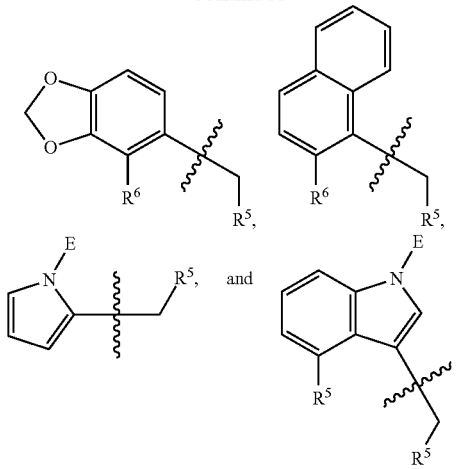

wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; E is a protecting group or a hydrogen atom; or a pharmaceutically suitable salt thereof.

Also disclosed herein are pharmaceutical and/or nutritional compositions for treating hyperglycemic, hyperlipidemic, or autoimmune disorders in mammals. The composition comprise an anti-hyperglycemic-effective, anti-hyperlipidemic, or anti-autoimmune effective amount of one or more the indole analogs disclosed herein, optionally in combination with a pharmaceutically suitable carrier.

More specifically disclosed and claimed herein are the following:

1. A method of making indoles, the method comprising: contacting a reactant of formula I:

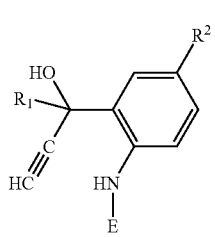
(I)

wherein E is a protecting group, —SO$_2$-Aryl, or —SO$_2$-substituted-Aryl; and $R^1$ and $R^2$ are independently selected from the group consisting of hydrogen, halo, $C_1$-$C_{12}$-alkyl, and aryl;

with a rhodium(I)-containing catalyst, in the presence or absence of an alpha-alkene-containing co-reactant, for a time and at a temperature to yield a product mixture comprising a compound selected from the group consisting of formula (II), (III), and (IV):

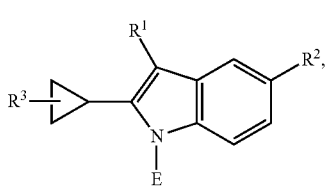
(II)

-continued

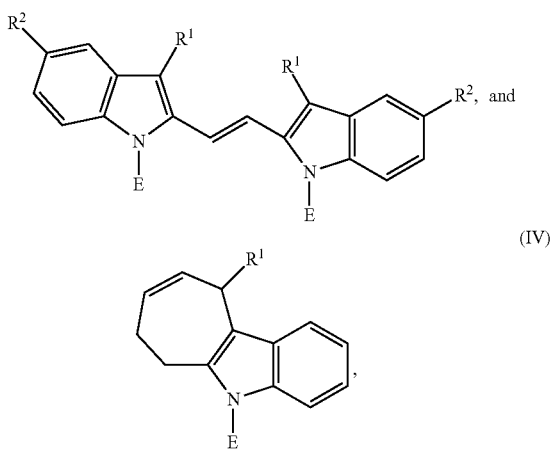

wherein $R^1$, $R^2$, and E are as defined previously, and $R^3$ is hydrogen in the absence of the alpha-alkene-containing co-reactant, and $R^3$ is a substituent corresponding to the alkene-containing co-reactant in the presence of the alkene-containing co-reactant.

2. The method of Claim 1, which yields a product mixture comprising a compound of formula (II).

3. The method of Claim 1, which yields a product mixture comprising a compound of formula (III).

4. The method of Claim 1, which yields a product mixture comprising a compound of formula (IV).

5. The method of Claim 1, conducted in the absence of the alpha-alkene-containing co-reactant.

6. The method of Claim 1, wherein the alkene-containing co-reactant is present and is selected from the group consisting of:

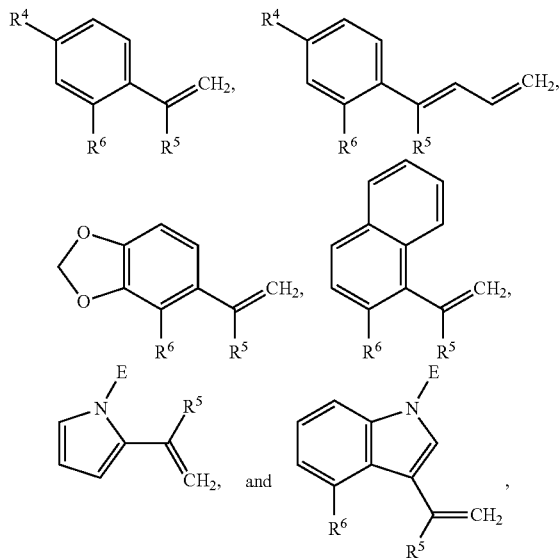

wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; and E is a protecting group.

7. The method of Claim 1, wherein the rhodium(I)-containing catalyst comprises $[Rh(CO)_2Cl]_2$.

8. The method of Claim 7, which yields a product mixture comprising a compound of formula (II).

9. The method of Claim 7, which yields a product mixture comprising a compound of formula (III).

10. The method of Claim 7, which yields a product mixture comprising a compound of formula (IV).

11. The method of Claim 7, conducted in the absence of the alpha-alkene-containing co-reactant.

12. The method of Claim 7, wherein the alkene-containing co-reactant is present and is selected from the group consisting of:

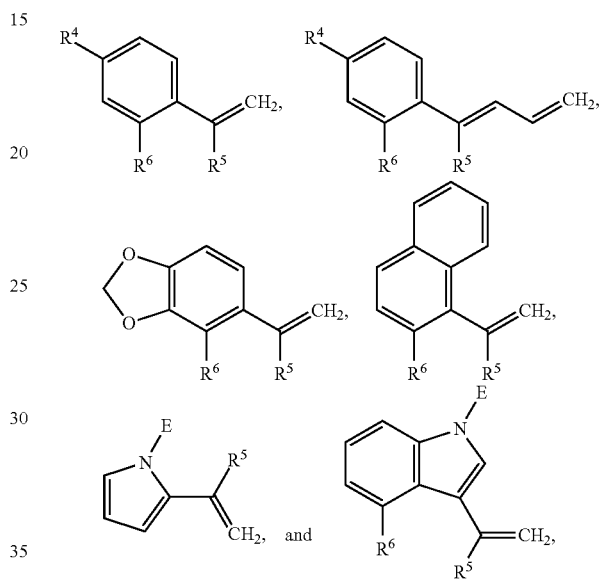

wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; and E is a protecting group.

13. The method of Claim 1, wherein the reactant of formula I is contacted with the catalyst in the presence of carbon monoxide.

14. The method of Claim 13, which yields a product mixture comprising a compound of formula (II).

15. The method of Claim 13, which yields a product mixture comprising a compound of formula (III).

16. The method of Claim 13, which yields a product mixture comprising a compound of formula (IV).

17. The method of Claim 13, conducted in the absence of the alpha-alkene-containing co-reactant.

18. The method of Claim 13, wherein the alkene-containing co-reactant is present and is selected from the group consisting of:

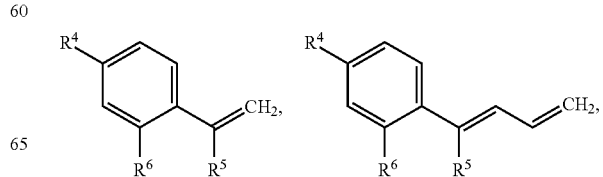

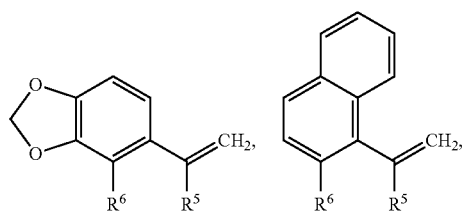

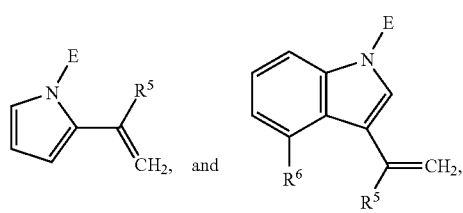

wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; and E is a protecting group.

19. A method of treating hyperglycemic, hyperlipidemic, or autoimmune disorders in mammals, the method comprising administering to a mammal an anti-hyperglycemic-effective, anti-hyperlipidemic-effective, or anti-autoimmune-effective amount of one or more compounds selected from the group consisting of:

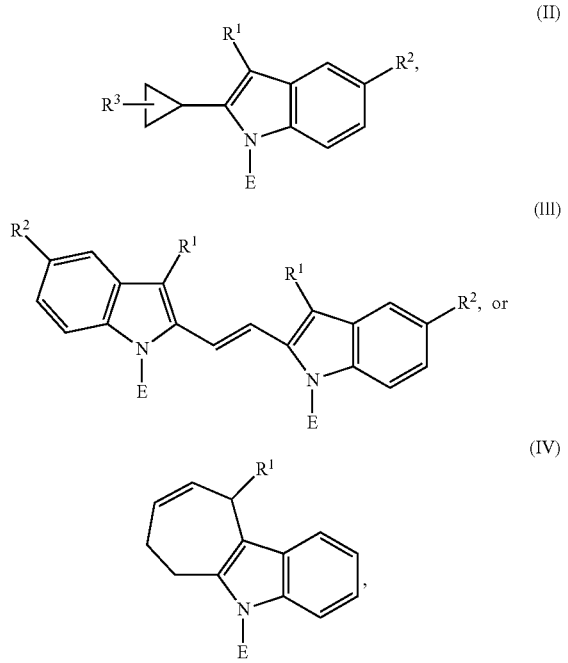

wherein $R^1$ and $R^2$ are independently selected from the group consisting of hydrogen, halo, $C_1$-$C_{12}$-alkyl, and aryl; and $R^3$ is selected from the group consisting of:

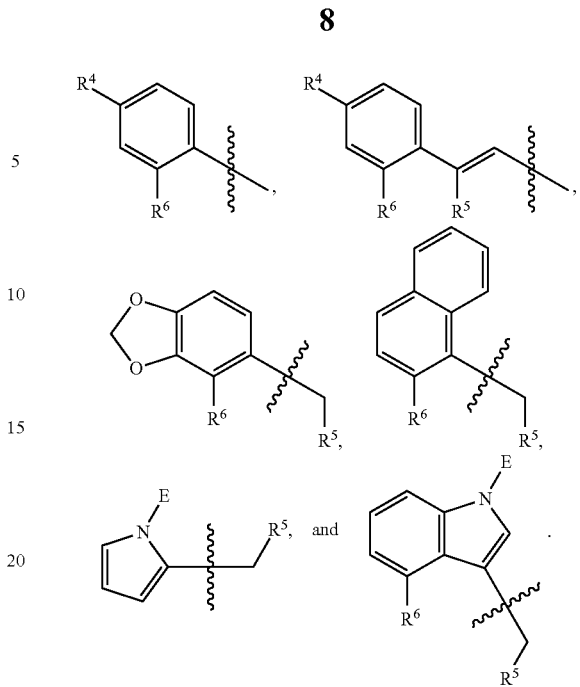

wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; E is a protecting group or a hydrogen atom;

or a pharmaceutically suitable salt thereof.

20. A pharmaceutical composition for treating hyperglycemic, hyperlipidemic, or autoimmune disorders in mammals, the composition comprising an anti-hyperglycemic-effective, anti-hyperlipidemic-effective, or anti-autoimmune-effective amount of one or more of the compounds recited in Claim 19, in combination with a pharmaceutically suitable carrier.

DETAILED DESCRIPTION

Abbreviations and Definitions

DCE=dichloroethane. HRMS (ESI)=high-resolution mass spectrometry (electrospray ionization). NMR=nuclear magnetic resonance. TLC=thin-layer chromatography.

Unless otherwise noted, the term "alkyl" whether used alone or as part of a substituent group, includes fully saturated straight, branched, and cyclic alkyl radicals. (That is, an alkyl is the radical formed by removing one hydrogen atom from a parent alkane.) For example, alkyl radicals include methyl, ethyl, propyl, isopropyl, butyl, isobutyl, sec-butyl, t-butyl, pentyl, heptyl, octyl and the like. $C_1$ to $C_{12}$ alkyls are preferred. Unless otherwise noted, "lower" when used with alkyl means a carbon chain composition of 1-6 carbon atoms. The term "alkenyl," refers to an alkenyl having at least one double bond. An alpha-alkene has a double bond at the alpha-position (or 1-position) carbon atom. An alkene is the parent compound of an alkenyl radical.

"Pharmaceutically-suitable salt"=any acid or base addition salt whose counter-ions are non-toxic to the patient in pharmaceutical doses of the salts, so that the beneficial inhibitory effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like.

A "protecting group" is any chemical moiety capable of selective addition to and removal from a reactive site to allow manipulation of a chemical entity at sites other than the reactive site. Many protecting groups are known in the art. A large number of protecting groups and corresponding chemical cleavage reactions are described in "Greene's Protective Groups in Organic Synthesis," ISBN-13: 978-1118057483, ©2014, John Wiley & Sons, Inc. (hereinafter "Greene"). Greene describes many nitrogen protecting groups, for example, amide-forming groups. For additional information on protecting groups, see also Kocienski, Philip J. "Protecting Groups," (Georg Thieme Verlag Stuttgart, New York, 1994), which is incorporated herein by reference. Typical nitrogen protecting groups described in Greene include benzyl ethers, silyl ethers, esters including sulfonic acid esters, carbonates, sulfates, and sulfonates. For example, suitable nitrogen protecting groups include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl) phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate(mesitoate)); carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-poly-benzoate, α-naphthoate, nitrate, alkyl N,N,N',N'-tetramethyl-phosphorodiamidate, n-phenylcarbamate, borate, 2,4-dinitrophenylsulfenate); or sulfonates (methanesulfonate(mesylate), benzenesulfonate, benzylsulfonate, tosylate, or triflate).

The more common of the amine-protecting groups have trivial abbreviations that are widely used in the literature and include: carbobenzyloxy (Cbz) group (removed by hydrogenolysis), p-methoxybenzyl carbonyl (Moz or MeOZ) group (removed by hydrogenolysis), tert-butyloxycarbonyl (BOC) group (common in solid phase peptide synthesis; removed by concentrated strong acid (such as HCl or $CF_3COOH$), or by heating to >80° C., 9-fluorenylmethyloxycarbonyl (FMOC) group (also common in solid phase peptide synthesis; removed by base, such as piperidine), acetyl (Ac) group (removed by treatment with a base), benzoyl (Bz) group (removed by treatment with a base), benzyl (Bn) group (removed by hydrogenolysis), carbamate group (removed by acid and mild heating), p-methoxybenzyl (PMB) (removed by hydrogenolysis), 3,4-dimethoxybenzyl (DMPM) (removed by hydrogenolysis), p-methoxyphenyl (PMP) group (removed by ammonium cerium(IV) nitrate (CAN)), tosyl (Ts) group (removed by concentrated acid and strong reducing agents), sulfonamide groups (Nosyl & Nps; removed by samarium iodide, tributyltin hydride.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth. In short, ranges as used herein are to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus.

Unless expressly stated to the contrary, "or" refers to an inclusive "or" and not to an exclusive "or." For example, a condition "A or B" is satisfied by any one of the following: A is true (or present) and B is false (or not present); A is false (or not present) and B is true (or present); and both A and B are true (or present).

The term "about" when used (for example) to modify the quantity of an ingredient or reactant, length, mass, pH, time, temperature, pressure, concentration, or any other numeric descriptor, refers to variation in the numerical quantity that can occur, for example, through typical measuring equipment and material handling procedures and the inherent errors (human and otherwise) used for making such measurements in the real world. The variations may arise from any source, without limitation, such as through through inadvertent error in these procedures (i.e., human error), through differences in the manufacture, source, or purity of the ingredients employed to make the compositions or carry out the methods, through the inherent sensitivity of the equipment used, etc. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

As described in full below, Rh(I)-carbenes were generated from propargyl alcohol derivatives via a dehydrative indole annulation. Depending on the choice of the electron-withdrawing group on the aniline nitrogen nucleophile, a cyclopropanation product or a dimerization product can be obtained, chemoselectively. Intramolecular hydroamidation occurred for the same type of propargylic alcohol derivatives when other transition metal catalysts were employed, such as gold-, silver-, platinum-, palladium-, and copper-based complexes.

In an effort to develop more general carbene precursors for the synthesis of diverse indole derivatives, it was found that indole annulation of propargylic alcohol 1 could produce Rh(I)-carbene 2, which underwent chemoselective cyclopropanation or dimerization to form products 3a and 3b, respectively, depending on the choice of the E-group. See Scheme 1. No dimerization product was found in the absence of external alkenes for precursor 1a; no cyclopropanation product was observed for precursor 1b in the presence of excess external alkenes.

Scheme 1. Divergent Reactivity of Rh(I)-Carbene Derived from Indole Annulation:

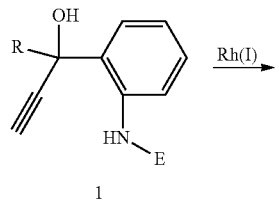

1a, E = Ts
1b, E = Boc

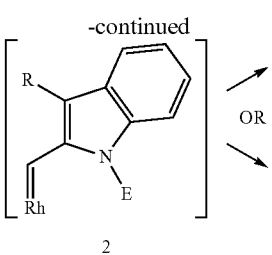

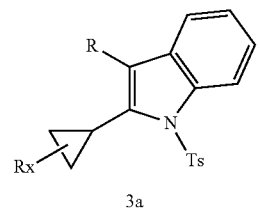

3a

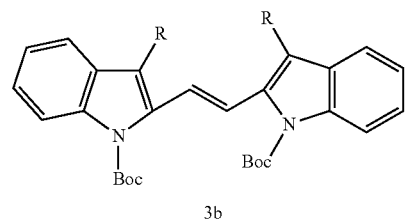

3b

Indole is one of the most abundant bioactive heterocycles in natural products and pharmaceutical agents.[9] Most previous indole synthesis focused on the construction of indole ring alone.[10] The present inventors, however, hypothesized that it would be more efficient to couple indole annulation with other transformations in a cascade manner. Propargylic alcohol 1 has been used by Chan extensively for various Au- and Ag-catalyzed tandem indole annulation and nucleophilic additions (Eq. 1).[11] Other catalysts, such as Pt-, Pd-, and Cu-based complexes can also mediate this process.[12] The Rh(I)-catalyst, however, is unique in promoting the formation of carbene 2, instead of hydroamidation product 4, and subsequent divergent transformations:

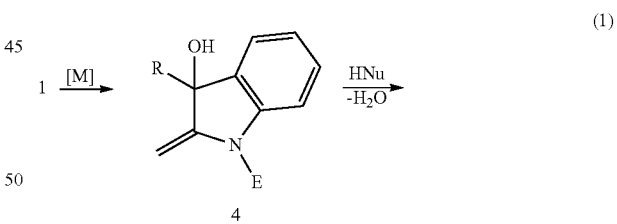

(M = Au-, Ag-, Pt-, Pd-, and Cu-based complexes)

Diazomethanes without an adjacent electron-withdrawing group are generally not very stable and those with an electron-rich aryl substituent are particularly difficult to prepare.[13] Indeed, the present inventors were not able to prepare the indolyl substituted diazomethane precursor for carbene 2 using known methods,[13] when they explored alternative cyclopropanation methods.[14] In the present disclosure, a tandem indole annulation of propargylic alcohol 1 followed by stereoselective cyclopropanation allows the construction of both the indole and cyclopropane ring systems, two of the most important rings in organic chemistry.[9,15]

By examining various transition metal catalysts that are known to mediate the cyclization of aniline 6a, it was found that Rh(I) complexes were able to promote the formation of both indole and cyclopropane and afford product 8a in the presence of alkene 7a (Eq. 2). Cationic Rh(I)-catalysts or neutral Rh(I)-catalysts without CO did not provide any desired product (entries 1-3, Table 1). High yield of product 8a could be obtained by using [Rh(CO)$_2$Cl]$_2$ complex as the catalyst in the presence or absence of a CO balloon (entries 4 and 5). When the amount of alkene was reduced from 2 equivalents to 1.2 equivalents, only slightly lower yield was observed (entry 6). No cyclopropanation products were formed when other metal complexes were employed (entries 7-10). In some cases, hydroamidation product 4 was observed, which is consistent with previous reports.[11-12]

Overall, generating the indolyl Rh(I) carbenes proceeds as follows:

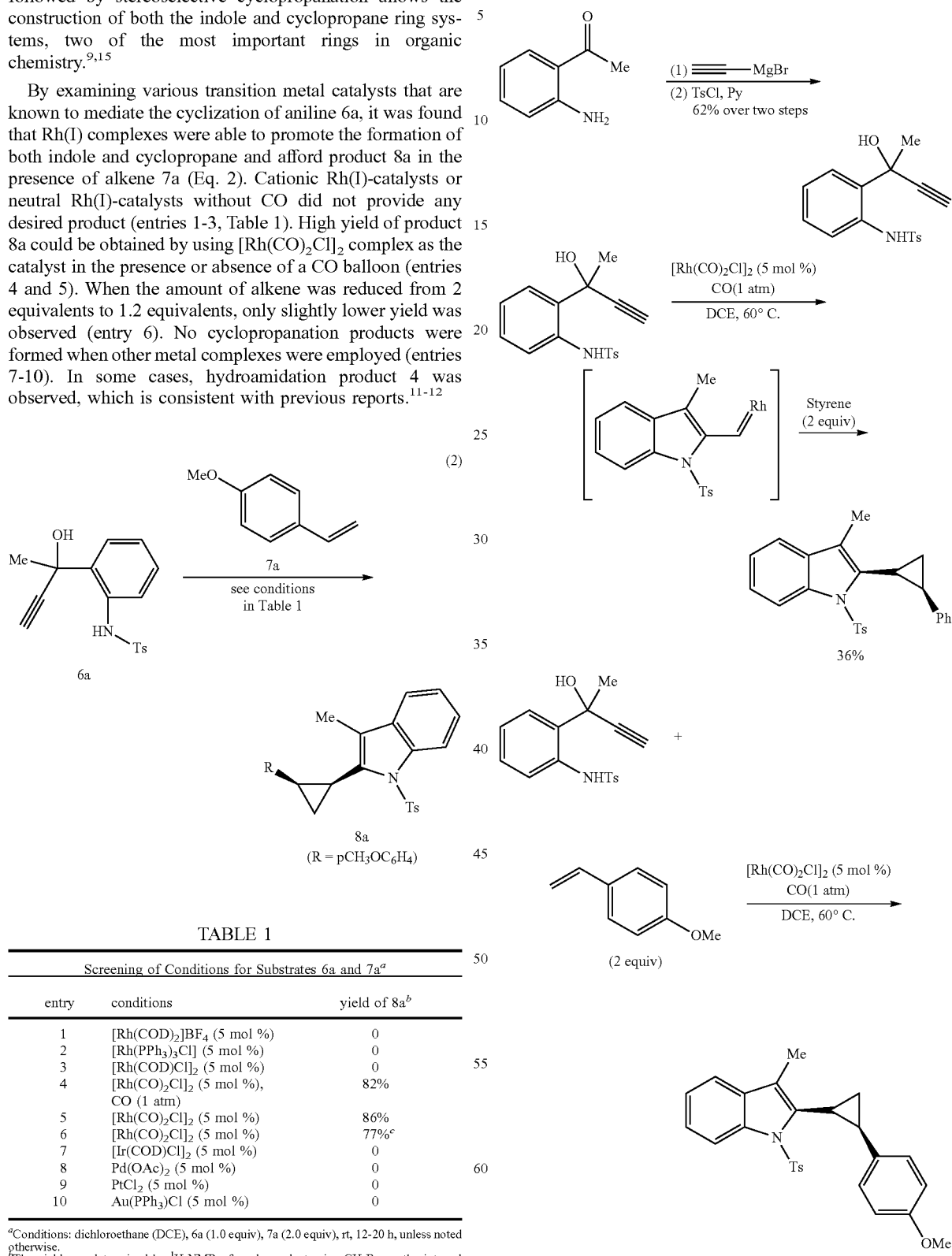

TABLE 1

Screening of Conditions for Substrates 6a and 7a[a]

| entry | conditions | yield of 8a[b] |
|---|---|---|
| 1 | [Rh(COD)$_2$]BF$_4$ (5 mol %) | 0 |
| 2 | [Rh(PPh$_3$)$_3$Cl] (5 mol %) | 0 |
| 3 | [Rh(COD)Cl]$_2$ (5 mol %) | 0 |
| 4 | [Rh(CO)$_2$Cl]$_2$ (5 mol %), CO (1 atm) | 82% |
| 5 | [Rh(CO)$_2$Cl]$_2$ (5 mol %) | 86% |
| 6 | [Rh(CO)$_2$Cl]$_2$ (5 mol %) | 77%[c] |
| 7 | [Ir(COD)Cl]$_2$ (5 mol %) | 0 |
| 8 | Pd(OAc)$_2$ (5 mol %) | 0 |
| 9 | PtCl$_2$ (5 mol %) | 0 |
| 10 | Au(PPh$_3$)Cl (5 mol %) | 0 |

[a]Conditions: dichloroethane (DCE), 6a (1.0 equiv), 7a (2.0 equiv), rt, 12-20 h, unless noted otherwise.
[b]The yield was determined by $^1$H NMR of crude product using CH$_2$Br$_2$ as the internal standard.
[c]7a (1.2 equiv).

TABLE 1a

Optimization of Reaction Conditions

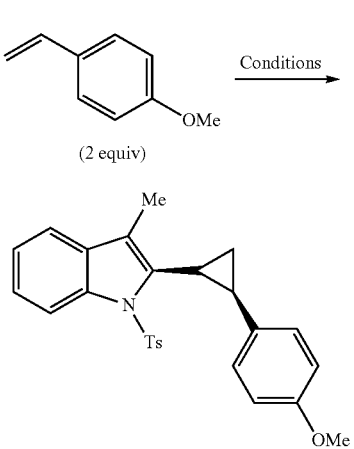

(2 equiv)

| Entry | Conditions | Yields [a] |
|---|---|---|
| 1 | [Rh(CO)$_2$Cl]$_2$ (5 mol %), CO (1 atm), DCE, rt, 12 h | 82% |
| 2 | [Rh(CO)$_2$Cl]$_2$ (5 mol %), DCE, rt, 12 h | 86% |
| 3 | [Rh(COD)$_2$Cl]$_2$ (5 mol %), DCE, rt, 12 h | 0 |
| 4 | Rh(COD)$_2$]BF$_4$ (5 mol %), DCE, rt, 12 h | 0 |
| 5 | [Rh(Ph$_3$P)$_3$Cl] (5 mol %), DCE, rt, 12 h | 0 |
| 6 | [Rh(CO)$_2$Cl]$_2$ (5 mol %), DCE, rt, 12 h | 77%[b] |
| 7 | [Ir(COD)$_2$Cl]$_2$ (5 mol %), DCE, rt, 12 h | 0 |
| 8 | PtCl$_2$, (5 mol %), DCE, 60° C., 12 h | 0 |
| 9 | AuCl(PPh$_3$) (5 mol %), DCE, 60° C., 12 h | 0 |

[a.] Yields were calculated based on $^1$H NMR using CH$_2$Br$_2$ as the internal standard.
[b] 1.2 equivalent alkene was used.

The scope of alkene co-reactant was then examined using propargylic alcohol 6a as the carbene precursor (Table 2). Various styrenes with a para-substituent participated in the cyclopropanation and yielded exclusively the cis-diastereoisomer (entries 1-4). The reactivity of electron-poor styrene is much lower than that of electron-rich styrene (entries 1 vs 5). Styrenes with multiple substituent or ortho-substituent could also be tolerated (entries 6 and 7). Trisubstituted cyclopropanes 8h-8j were successfully prepared from 1,1-disubstituted alkenes (entries 8-10). Notably, free alcohols in 7i and 7j were tolerated under the standard conditions. Other arenes such as pyrrole, naphthalene, and indole could also be introduced to the diaryl cyclopropane products (entries 11-13). Unfortunately, 1,2-disubstituted alkene 7n did not participate in the cyclopropanation. No cyclopropanation was observed by using alkenes with just an alkyl substituent including both electron-rich vinyl ethers and electron-poor enones.

The scope of the propargylic alcohols was also explored. See Table 3. The aryl sulfonyl group does not have obvious effect on the tandem annulation/cyclopropanation (entries 1-5). The R$^1$ group can be a hydrogen or other alkyl groups (entries 6-8). Substituents can be introduced to the benzene ring of substrate 9 (entries 9 and 10). Notably, aryl bromide in 9i can be tolerated for Rh-catalyzed reactions.

Diene 11 participated in the cyclopropanation and afford vinylcyclopropane 12, which could undergo Cope rearrangement to yield cyclohepta[b]indole 14 (Scheme 2).[16] Indole fused with a seven-membered ring is present in a number of natural products[17] and bioactive pharmaceutical agents.[18]

Scheme 2. Sequential Indole Annulation, Cyclopropanation, and Cope Rearrangement:

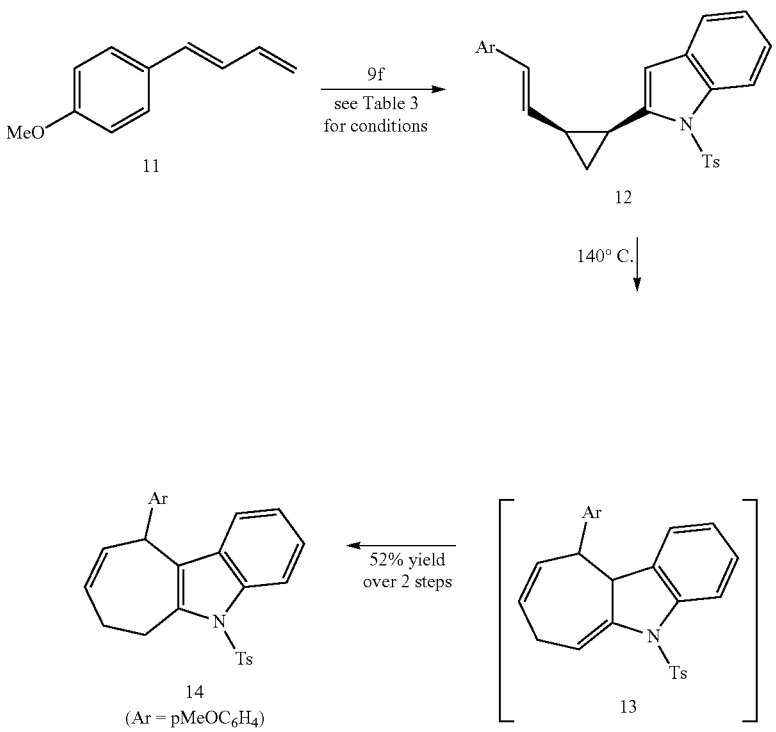

TABLE 2

Scope of Alkenes for the Tandem Indole Annulation/Cyclopropanation with 6a[a]

| entry | substrate 7 | product 8 (dr)[b] | yield[c] |
|---|---|---|---|
| 1 | 7a, R = MeO | 8a (20:1) | 80% |
| 2 | 7b, R = H | 8b (20:1) | 48% |
| 3 | 7c, R = Me | 8c (20:1) | 68% |
| 4 | 7d, R = tBu | 8d (20:1) | 70% |
| 5 | 7e, R = CF$_3$ | 8e | 20%[b] |
| 6 | 7f, | 8f, (20:1) | 78% |
| 7 | 7g, | 8g, (20:1) | 70% |
| 8 | 7h, R$^1$ = Me, R$^2$ = H | 8h, (20:1) | 63% |
| 9 | 7i, R$^1$ = CH$_2$OH, R$^2$ = H | 8i, (20:1) | 52% |
| 10 | 7j, R$^1$ = CH$_2$OH, R$^2$ = MeO | 8j, (20:1) | 87% |
| 11 | 7k | 8k (20:1) | 64% |

TABLE 2-continued

Scope of Alkenes for the Tandem Indole Annulation/Cyclopropanation with 6a[a]

| entry | substrate 7 | product 8 (dr)[b] | yield[c] |
|---|---|---|---|
| 12 | 7l | 8l (20:1) | 53% |
| 13[d] | 7m | 8m (20:1) | 60% |
| 14 | 7n | — | 0% |

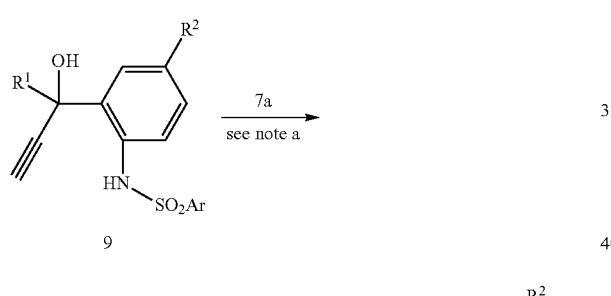

[a]Conditions: [Rh(CO)$_2$Cl]$_2$ (5 mol %), DCE, 6a (1.0 equiv), 7 (2.0 equiv), rt, 12-20 h, unless noted otherwise.
[b]Determined by $^1$H NMR of crude product using CH$_2$Br$_2$ as the internal standard.
[c]Isolated yield.
[d]Substrate 9f (Table 3) was employed in this case.

TABLE 3

Scope of Propargylic Alcohols for the Tandem Indole Annulation/Cyclopropanation[a]

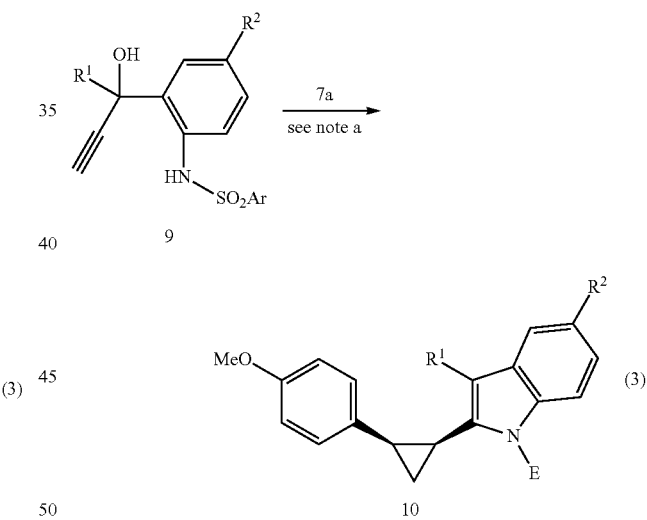

| entry | substrate 9 | product 10 (dr)[b] | yield[c] |
|---|---|---|---|
| 1 | 9a, R$^1$ = Me, R$^2$ = H, Ar = Ph | 10a (20:1) | 72% |
| 2 | 9b, R$^1$ = Me, R$^2$ = H, Ar = 4-FC$_6$H$_4$ | 10b (20:1) | 77% |
| 3 | 9c, R$^1$ = Me, R$^2$ = H, Ar = 4-tBuC$_6$H$_4$ | 10c (20:1) | 72% |
| 4 | 9d, R$^1$ = Me, R$^2$ = H, Ar = 4-MeOC$_6$H$_4$ | 10d (20:1) | 73% |
| 5 | 9e, R$^1$ = Me, R$^2$ = H, Ar = 1-naphthyl | 10e (20:1) | 75% |
| 6 | 9f, R$^1$ = R$^2$ = H, Ar = 4-MeC$_6$H$_4$ | 10f (20:1) | 66% |
| 7 | 9g, R$^1$ = Et, R$^2$ = H, Ar = 4-MeC$_6$H$_4$ | 10g (5:1) | 81% |
| 8 | 9h, R$^1$ = nBu, R$^2$ = H, Ar = 4-MeC$_6$H$_4$ | 10h (5:1) | 77% |
| 9 | 9i, R$^1$ = Me, R$^2$ = Br, Ar = 4-MeC$_6$H$_4$ | 10i (20:1) | 71% |
| 10 | 9j, R$^1$ = Me, R$^2$ = Ph, Ar = 4-MeC$_6$H$_4$ | 10j (20:1) | 75% |

[a]Conditions: [Rh(CO)$_2$Cl]$_2$ (5 mol %), DCE, 9 (1.0 equiv), 7a (2.0 equiv), rt, 12-20 h, unless noted otherwise.
[b]Determined by $^1$H NMR of crude product using CH$_2$Br$_2$ as the internal standard.
[c]Isolated yield.

In addition to various arylsulfonyl groups in Table 3, the effect of other electron-withdrawing groups on the aniline nucleophile for the tandem annulation/cyclopropanation was also explored. Under the standard conditions in Table 3, no cyclopropanation product was observed for substrate 15a in the presence of different styrenes. Instead, trace amount of dimeric indole 16a was obtained in the presence or absence of styrenes (entry 1, Table 4). The yield of the dimeric indole was improved dramatically by simply attaching a CO balloon to the reaction flask (entry 2). Under these condition, the dimeric indole for substrate 6a with a tosyl group on the nitrogen (entry 4, Table 1) was not observed.

Using the above-noted reaction conditions, the following cyclopropyl indole compounds were made at the stated yields:

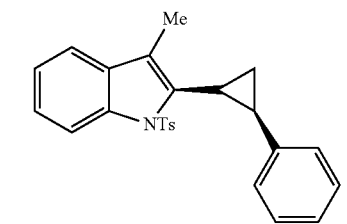
48%

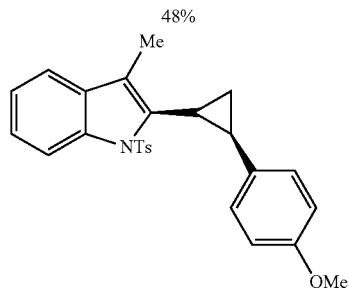
80%

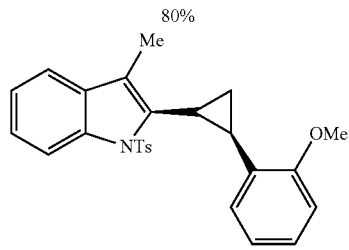
70%

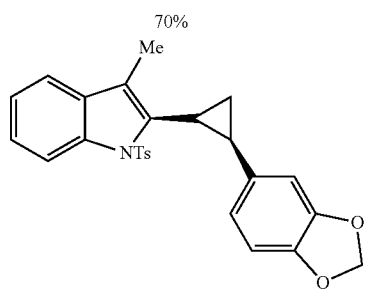
78%

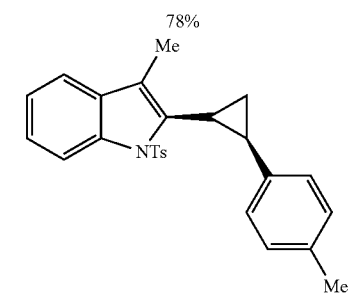
68%

-continued

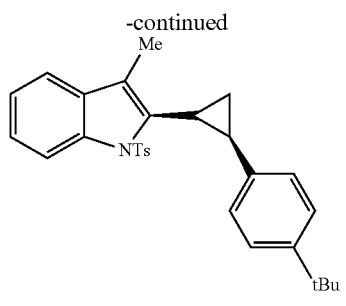
70%

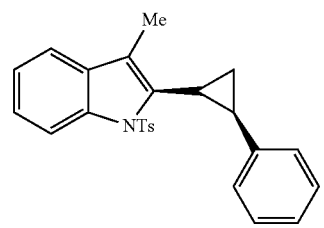
48%

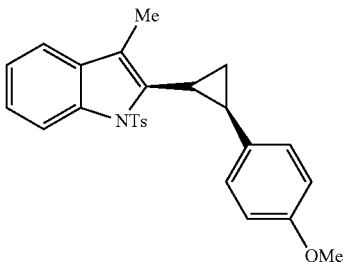
80%

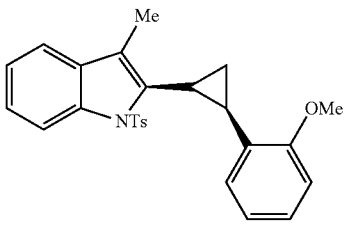
70%

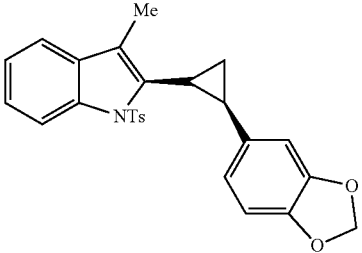
78%

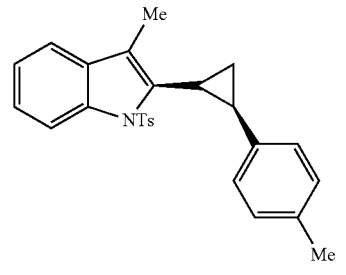
68%

-continued
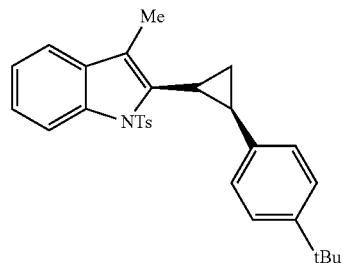
70%
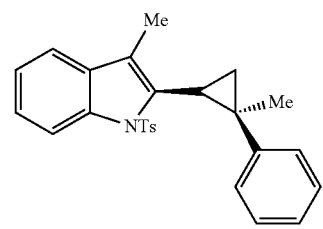
63%
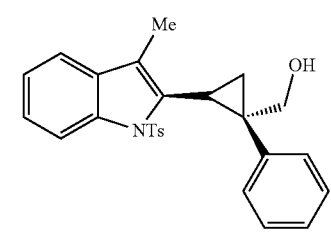
52%
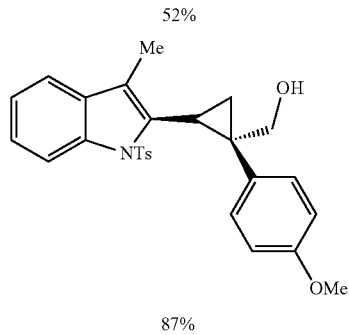
87%
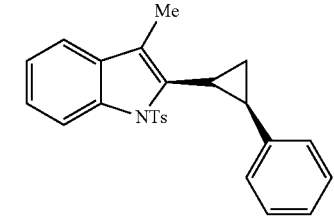
48%
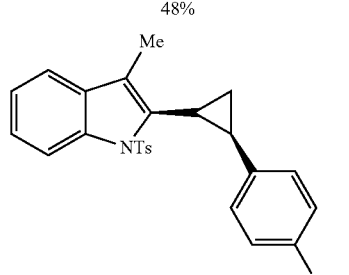
80%
-continued
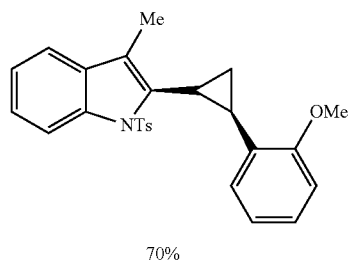
70%
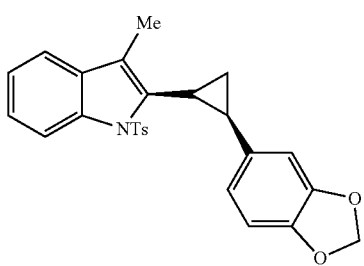
78%
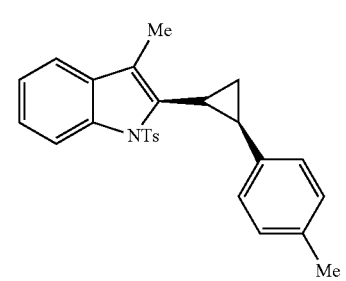
68%
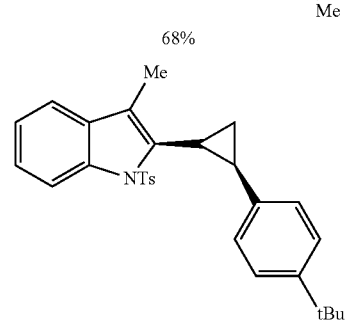
70%
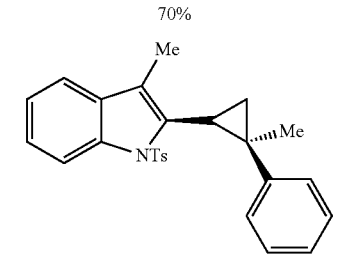
63%
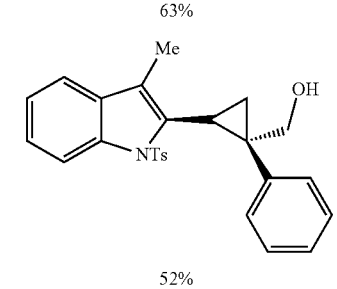
52%

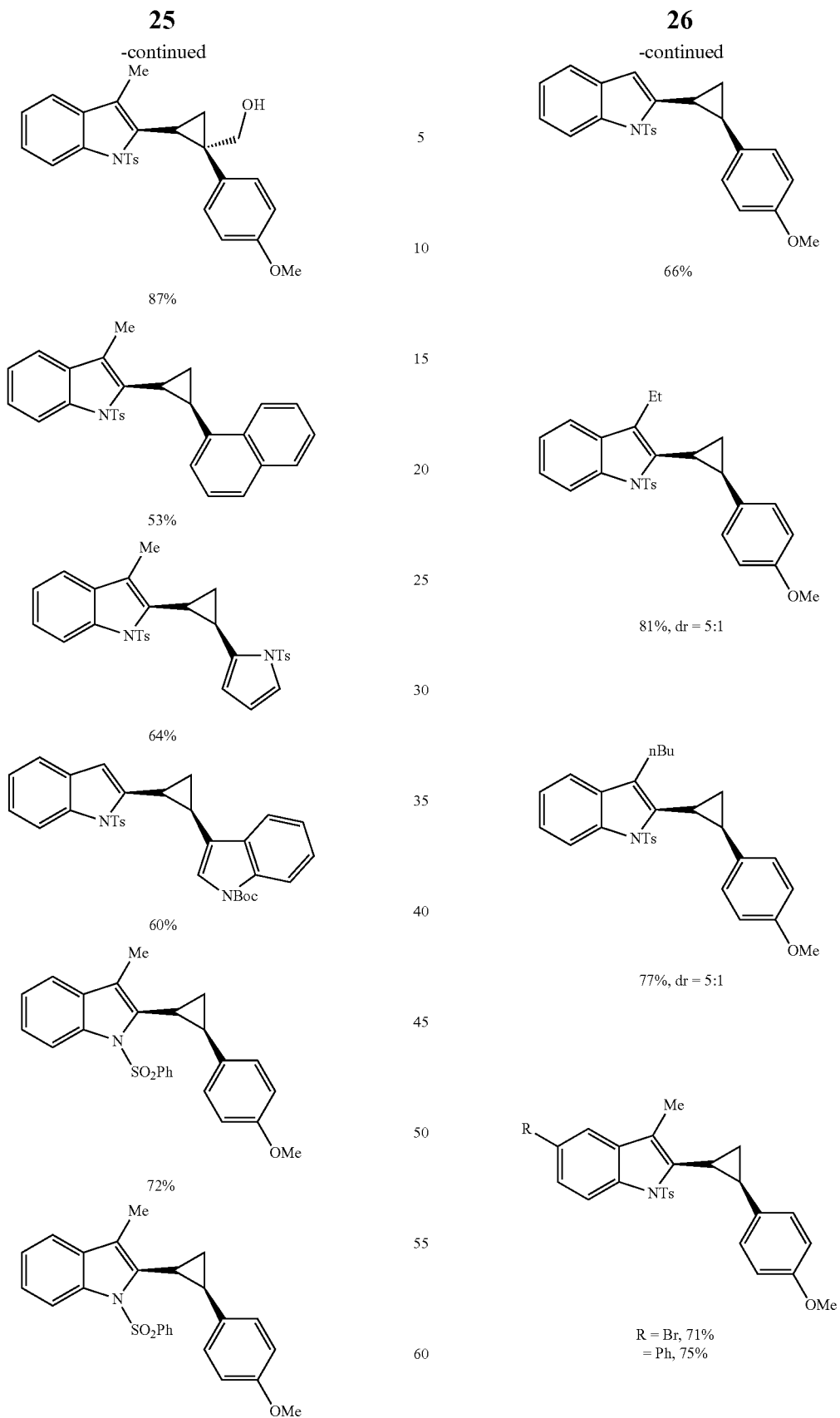
As shown in Table 3a, cyclopropanation can also be accomplished enantioselectively:

TABLE 3a

Enantioselective Cyclopropanation

[structure: HO, Me, alkyne-substituted aniline with NHTs] + [4-methoxystyrene (2 equiv)]

[Rh(CO)₂Cl]₂ (5 mol %)
Ligand (10 mol %)
───────────────→
DCE, 60° C.

[product: indole-cyclopropane with Me, NTs, and 4-OMe-phenyl groups]

dr > 20:1

| Entry | Ligands | Yields | ee |
|---|---|---|---|
| 1 | n = 1, Ar = C₆H₅ | 56% | 0 |
| 2 | n = 1, Ar = 3,5-CF₃C₆H₃ | 53% | 38 |
| 3 | n = 1, Ar = C₆H₅ | 67% | 52% |
| 4 | n = 2, Ar = C₆H₅ | 65% | 60% |
| 5 | n = 3, Ar = C₆H₅ | 62% | 35% |

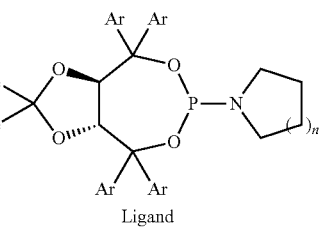

Ligand

Dimerization of carbenes is generally a low yield side reaction in transformations involving this reactive intermediate with a few exceptions.[19] Given the high yield of product 16a and the potential utility of indole derivatives, the scope of the indole dimerization (Table 5) was further explored. In addition to Boc-group, other alkoxy carbonyl groups (entries 2 and 4), acetyl (entry 3), and dimethylaminocarbonyl group (entry 5) also facilitated the formation of dimer 16. It is also interesting to note that the carbene intermediate cannot be trapped by even an intramolecularly tethered alkene (entry 4). The R¹ substituent can be a hydrogen, ethyl, isopropyl, butyl, phenyl, etc. (entries 6-10). Dimeric indoles with substituents on the benzene ring could also be prepared (entries 11 and 12). As shown in the Examples, the E- and Z-isomers can be separated by column chromatography in many cases. The structures of the dimeric indoles were unambiguously determined by X-ray analysis of E-16b and Z-16b. It was also found that Z-16a could be isomerized completely to E-16a under thermal conditions.

TABLE 4

Screening of Conditions for Dimerization of 11a[a]

[structure 15a: aryl compound with OH, Me, alkyne, NHBoc]

─conditions→

[structure 16a: bis-indole dimer with Boc, Me groups, connected by alkene] (4)

| entry | conditions | yield and E/Z ratio of 12a[b] |
|---|---|---|
| 1 | [Rh(CO)₂Cl]₂ (5 mol %), DCE, 60° C., 12 h | trace |
| 2 | [Rh(CO)₂Cl]₂ (5 mol %), CO (1 atm) DCE, 60° C., 12 h | 86% (1.4:1) |
| 3 | [Rh(COD)Cl]₂ (5 mol %), CO (1 atm) DCE, 60° C., 12 h | 71% (1:1) |
| 4 | [Rh(COD)₂]BF₄ (5 mol %) | 0 |
| 5 | [Rh(COD)₂]BF₄ (5 mol %), CO (1 atm) | trace |
| 6 | [Ir(COD)Cl]₂ (5 mol %), CO (1 atm) | 0 |
| 7 | Pd(OAc)₂ (5 mol %), CO (1 atm) | 0 |
| 8 | PtCl₂ (5 mol %), CO (1 atm) | 0 |
| 9 | Au(PPh₃)Cl (5 mol %), CO (1 atm) | 0 |

[a]Conditions: dichloroethane (DCE), 15a, 60° C., 10 h, unless noted otherwise.
[b]The yield and E/Z ratio were determined by ¹H NMR of crude product using CH₂Br₂ as the internal standard.

TABLE 5

Scope of Indole Dimerization[a]

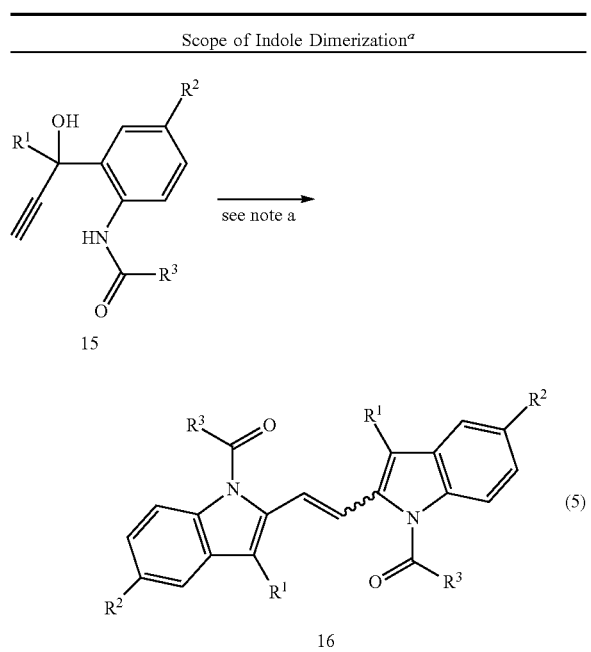

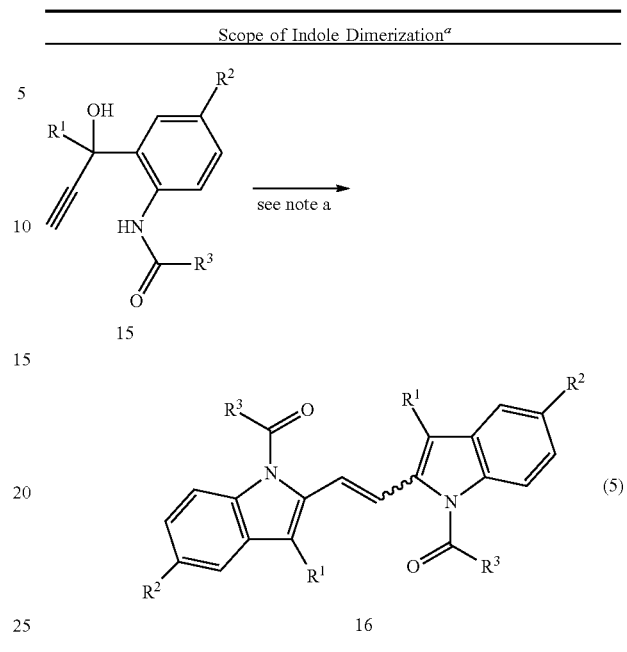

| entry | substrate 15 | product (E/Z)[b] | 16 yield[c] |
|---|---|---|---|
| 1 | 15a, R¹ = Me, R² = H, R³ = tBuO | 16a (1.4:1) | 81% |
| 2 | 15b, R¹ = Me, R² = H, R³ = MeO | 16b (1.2:1) | 81% |
| 3 | 15c, R¹ = Me, R² = H, R³ = Me | 16c (1.1:1) | 75% |
| 4 | 15d, R¹ = Me, R² = H, R³ = CH₂=CHCH₂CH₂ | 16d (1.4:1) | 82% |
| 5 | 15e, R¹ = Me, R² = H, R³ = Me₂N | 16e (2:1) | 55%[d] |
| 6 | 15f, R¹ = R² = H, R³ = tBuO | 16f (1.2:1) | 88% |
| 7 | 15g, R¹ = Et, R² = H, R³ = tBuO | 16g (1.3:1) | 82% |
| 8 | 15h, R¹ = iPr, R² = H, R³ = tBuO | 16h (1.3:1) | 74% |
| 9 | 15i, R¹ = nBu, R² = H, R³ = tBuO | 16i (1.5:1) | 80% |
| 10 | 15j, R¹ = Ph, R² = H, R³ = tBuO | 16j (1.1:1) | 60% |
| 11 | 15k, R¹ = Me, R² = Br, R³ = tBuO | 16k (1.3:1) | 92% |
| 12 | 15l, R¹ = Me, R² = Ph, R³ = tBuO | 16l (1.3:1) | 93% |

[a]Conditions: [Rh(CO)₂Cl]₂ (5 mol %), CO (1 atm), dichloroethane (DCE), 15a, 60° C., 10 h, unless noted otherwise. unless noted otherwise.
[b]Determined by ¹H NMR of crude product using CH₂Br₂ as the internal standard.
[c]Isolated yield of two isomers.
[d]Isolated yield of E-isomer.

The mechanism of the indole annulation/cyclopropanation or dimerization is proposed in Scheme 3. Coordination of the metal catalyst to alkyne in propargylic alcohol 1 will induce nucleophilic attack of the aniline nitrogen to form adduct 17.[7] Protonation to form the hydroamidation product 4 occurred for most n-acidic transition metals. In the case of Rh(I) complexes with a CO ligand, elimination of water occurred to yield carbene intermediate 18, which can undergo either cyclopropanation or dimerization depending on the nature the E-group. We propose that the chemoselectivity arise from the ability of the carbonyl group in 18b to coordinate to Rh(I)-carbenes. This type of coordination was also proposed by Tanaka in their Rh-catalyzed cascade 1,2-acyloxy migration of propargylic esters/intermolecular cyclopropanation.[6] The cis-selective cyclopropanation is consistent with gold-catalyzed 1,2-acyloxy migration of propargylic esters/intermolecular cyclopropanation.[20]

Scheme 3. Proposed Mechanism for the Formation of Rh(I)-Carbenes and Their Divergent Reactivity

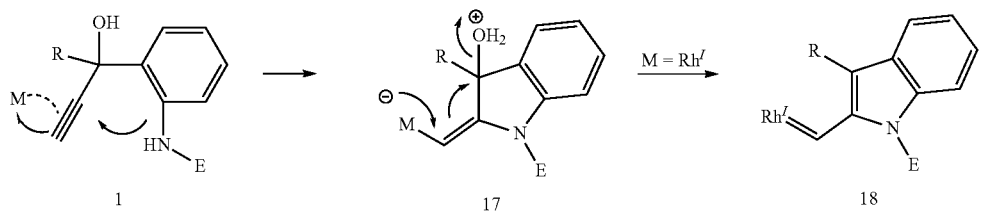

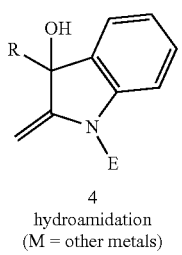

4
hydroamidation
(M = other metals)

-continued

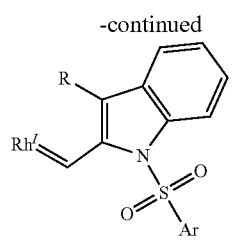

18a

↓ cyclopropanation

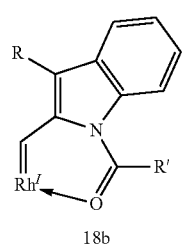

18b

↓ dimerization

In summary, various cyclopropanes with cis-1,2-diaryl substituents were prepared stereoselectively from propargylic alcohol derivatives via a tandem indole annulation and cyclopropanation. The enantioselective version of this cascade process is currently under investigation in our laboratory. Computational studies are also ongoing to elucidate the origin of the intriguing chemoselectivity.

Nutritional Compositions:

The present disclosure includes nutritional compositions. Such compositions include any food or preparation for human consumption (including for enteral or parenteral consumption) which when taken into the body (a) serve to nourish or build up tissues or supply energy and/or (b) maintain, restore or support adequate nutritional status or metabolic function.

The nutritional composition comprises at least one indol derivative as described herein and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany hyperglycemic and hyperlipidemic metabolic conditions. As a general proposition, the compositions contain a sufficient amount of one or more of the indole compounds to alleviate, remediate, attenuate, or otherwise reduce the hyperglycemic and/or hyperlipidemic metabolic condition(s) in the subject when taken on a prescribed schedule.

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition include but are not limited to soy proteins, electrodialysed whey, electrodialysed skim milk, milk whey, or the hydrolysates of these proteins.

With respect to vitamins and minerals, the following may be added to the nutritional compositions described herein: calcium, phosphorus, potassium, sodium, chloride, magnesium, manganese, iron, copper, zinc, selenium, iodine, and Vitamins A, E, D, C, and the B complex. Other such vitamins and minerals may also be added.

Examples of nutritional compositions disclosed herein include but are not limited to infant formulas, dietary supplements, dietary substitutes, and rehydration compositions. Nutritional compositions of particular interest include but are not limited to those utilized for enteral and parenteral supplementation for infants, specialist infant formulas, supplements for the elderly, and supplements for those with hyperglycemia.

The nutritional composition of the present invention may also be added to food even when supplementation of the diet is not required. For example, the composition may be added to food of any type including but not limited to margarines, modified butters, cheeses, milk, yoghurt, chocolate, candy, snacks, salad oils, cooking oils, cooking fats, meats, fish and beverages.

In a preferred version, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to indole analogs described herein, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. An enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®-brand and Ensure®-brand formulas from Ross Products Division, Abbott Laboratories, Columbus, Ohio). An indole analog produced in accordance with the present disclosure may be added to commercial formulas of this type.

The energy density of the nutritional compositions in liquid form may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

Pharmaceutical Compositions:

Also disclosed herein are pharmaceutical compositions comprising one or more of the indole analogs or a pharmaceutically suitable salt thereof as described herein. More specifically, the pharmaceutical composition may comprise one or more of the indole analogs, as well as a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectible, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, indole analogs produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant indole analog.

For intravenous administration, the indole analogs may be incorporated into commercial formulations such as Intralipid-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative indole analog as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical stated of the subject being treated. The dosage of the composition to be administered to the patient may be determined by one of ordinary skill in the art and depends upon various factors such as weight of the patient, age of the patient, immune status of the patient, etc., and is ultimately at the discretion of the medical professional administering the treatment.

With respect to form, the composition may be, for example, a solution, a dispersion, a suspension, an emulsion or a sterile powder which is then reconstituted. The composition may be administered in a single daily dose or multiple doses.

The present disclosure also includes methods of treating hyperglycemic, hyperlipidemic, and autoimmune disorders in mammals, including humans, by administering an anti-hyperglycemic-effective, anti-hyperlipidemic, and/or anti-autoimmune amount of one or more the indole analogs described herein. In particular, the compositions of the present invention may be used to treat diabetic conditions of any and all description. Additionally, the compositions of the present invention may also be used to prevent the apoptotic death of β cells in the pancreas. To the extent the compositions impart a feeling of satiation, the compositions may also be used to treat obesity and to ease weight loss.

It has also been found that the present indole analogs modify the activity of proprotein convertase subtilisin kexin type 9 (PCSK9). Thus, the compounds disclosed herein are useful to treat hyperlipidemia and thus also to inhibit coronary artery disease. PCSK9 was first identified in 2003, Seidah et al. (2003) *Proc. Natl. Acad. Sci. U.S.A.* 100:928. The PCSK9 enzyme is encoded by the PCSK9 gene; a proprotein convertase activates the enzyme. Compounds that block, inhibit, or otherwise attenuate PCSK9 secretion and/or activity can lower low density lipoprotein cholesterol (LDL-C) levels in mammals. Thus, PCSK9 constitutes an attractive therapeutic target for the treatment of hyperlipidemia in mammals, including in humans. A number of monoclonal antibodies that bind to PCSK9 are in clinical trials as of 2014. These include evolocumab (Amgen), 1D05-IgG2 (Merck) and alirocumab (Aventis/Regeneron).

PCSK9 belongs to the proteinase K subfamily of secretory proteases. This protein plays a major regulatory role in cholesterol homeostasis. PCSK9 regulates plasma LDL-cholesterol (LDL-C) levels by directing LDL receptor (LDLR) to lysosomal degradation, resulting in reduced LDL clearance and accumulation of LDL in the circulation. Gain-of-function mutations of PCSK9 lead to hyperlipidemia and premature coronary artery disease in humans. In contrast, loss-of-function mutations of PCSK9 are associated with lower levels of LDL and protection from coronary artery disease. The therapeutic antibodies noted above display impressive efficacy in LDL lowering either as a monotherapy or in a combination therapy with statins. Given this strong clinical validation, small molecule inhibitors of PCSK9 are expected to display similar activity.

PCSK9 expression is actively regulated at transcription levels. Statins are known to stimulate PCSK9 transcription which in turn curbs the efficacy of statins in LDL lowering in humans. A few other molecules, including berberine and oncostatin, have been shown to suppress PCSK9 transcription, which in turn contributes to the hypolipidemic effects of these agents. A number of primary and secondary assays to measure PCSK9 secretion/modulation in response to putative active agents are known. Primary assays: PCSK9 Secretion HepG2 SP/CRC (% Inhibition/$IC_{50}$); PCSK9 Secretion Cell Health HepG2 SP/CRC (% Inhibition/$IC_{50}$); and Metabolic Luciferase Reporter Assay CRC ($IC_{50}$). Secondary assays: PCSK9 ELISA HepG2 CRC ($IC_{50}$); ApoA-1 ELISA HepG2 CRC ($IC_{50}$), and Profiling Biochemical Activity—Kinase Panel SP/CRC (% Efficacy/$IC_{50}$). All of these assays are publicly accessible via Lilly's Open Innovation Drug Discovery program (as well as other sources).

Compounds disclosed herein have been shown to be selective inhibitors of PCSK9 secretion in HepG2 cells.

TABLE 6

Selective Inhibitors of PCSK9 Secretion in HepG2 Cells
A) selective inhibitor

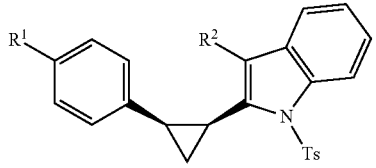

1a, $R^1$ = H, $R^2$ = Me
1b, $R^1$ = OMe, $R^2$ = Me
1c, $R^1$ = OMe, $R^2$ = Et

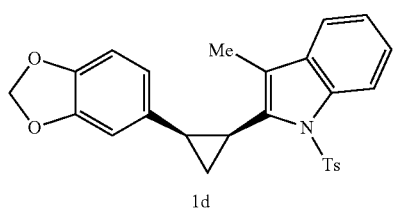 [SMILES: Cc1ccc(S(=O)(=O)n2c([C@H]3C[C@H]3c3ccc4c(c3)OCO4)c(C)c3ccccc32)cc1]

1d

B) $IC_{50}s$

| compounds | $IC_{50}$-A inhibition of PCSK9 secretion | $IC_{50}$-B cytotoxicity | $IC_{50}$-C non-selective inhibition at protein secretion |
|---|---|---|---|
| 1a | 21 uM | — | — |
| 1b | 1.8 uM | >50 uM | >50 uM |
| 1c | 0.7 uM | >50 uM | >50 uM |
| 1d | 9.9 uM | >50 uM | >50 uM |

Similarly, the present indole compounds also modify the activity of glucagon-like peptide 1 (GLP-1), which plays a critical role in hyperglycemia and diabetes in humans. Glucagon-like peptide 1 (GLP-1) is derived from transcription of the proglucagon gene followed by post-translational modifications of proglucagon to the following biologically active peptides: GLP-1 (7-37) and GLP-1 (7-36)-NH2. GLP-1 secretion by ileal L cells is dependent on the presence of nutrients in the lumen of the small intestine. GLP-1 is a potent anti-hyperglycemic hormone that induces glucose-dependent insulin secretion and suppresses glucagon secretion. The glucose dependency of this mechanism is particularly important because GLP-1 does not stimulate insulin secretion and cause hypoglycemia when plasma glucose concentrations are in the normal fasting range.

GLP-1 secretion is measured using an ELISA designed to detect the appropriate forms of GLP-1 secreted from these cells. See, for example, Gareth E. Kim and Patricia L. Brubaker (December 2006) "Glucagon-Like Peptide 1 Secretion by the L-Cell," *Diabetes:* 55 (supplement 2).

It has also been found that the present indole analogs inhibit the secretion of IL-17. The present compounds are thus useful to treat autoimmune disorders such as (but not limited to) arthritis, multiple sclerosis, psoriasis, and inflammatory bowel disease. The IL-17 pathway plays an essential pathological role in many autoimmune diseases including arthritis, multiple sclerosis, psoriasis, and inflammatory bowel disease. IL-17 is produced and secreted by at least two classes of lymphocytes, δγ and CD4+ T cells (Th17). The orphan nuclear receptor RORg is required for the differentiation of Th17 cells where over-expression in human and rodent T cells induces transcripts found in Th17 cells encoding key cytokines for the IL23 receptor and chemokines for the CCR6 receptor. In addition to RORg, recent global analysis of transcription factors has highlighted the molecular complexity of the Th17 differentiation program.

Active compounds are identified by measuring their ability to inhibitor IL17 secretion from human peripheral blood mononuclear cells (PBMCs) following stimulation of memory T cells by IL23, anti-CD3, and anti-CD28. See M. Ciofani, et al (2012) "A validated regulatory network for Th17 cell specification." *Cell,* 151:289-303.

It should be noted that the above-described pharmaceutical and nutritional compositions may be utilized in connection with non-human animals, both domestic and non-domestic, as well as humans.

EXAMPLES

The following Examples are included solely to provide a more complete description of the compounds disclosed and claimed herein. The Examples do not limit the scope of the claims in any fashion.

General Experimental Procedures for Cyclopropanation:

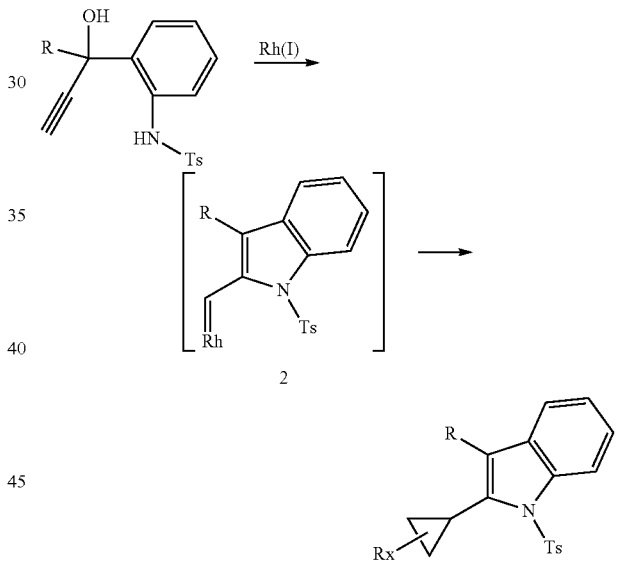

To an oven-dried flask was added propargylic alcohol substrate (0.1 mmol), alkenes (0.2 mmol), anhydrous DCE (2 ml), and $[Rh(CO)_2Cl]_2$ (0.005 mmol). The flask was degassed and stirred at room temperature. The reaction was monitored by TLC. After the reaction was completed, the solvent was evaporated and the residue was purified by flash column chromatography.

General Experimental Procedures for Dimerization:

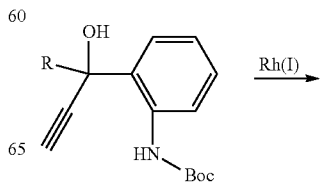

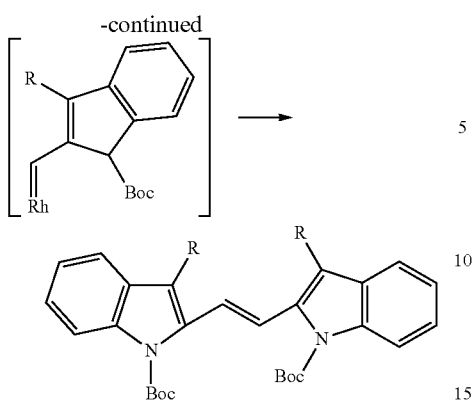

To an oven-dried flask was added propargylic alcohol substrate (0.2 mmol), anhydrous DCE (4 ml), and [Rh(CO)$_2$Cl]$_2$ (0.01 mmol). The flask was degassed and filled with a CO atmosphere (1 atm). The oil bath was heated to 60° C. The reaction was monitored by TLC. After the reaction was completed, the solvent was evaporated and the residue was purified by flash column chromatography.

General Procedure for the Synthesis of Cyclohepta[b]Indole:

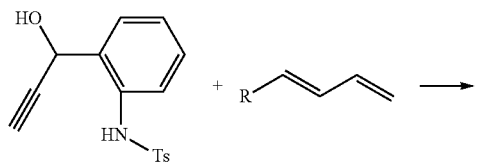

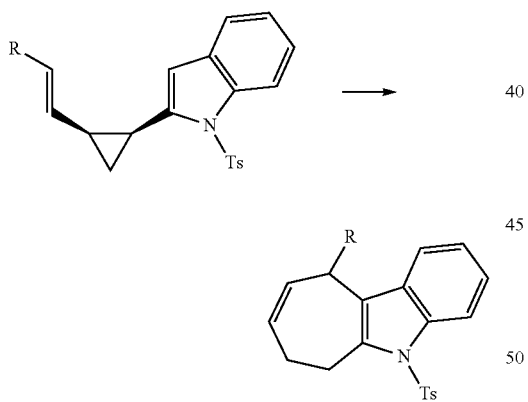

To an oven-dried flask was added substrate propargylic alcohol (30 mg, 0.1 mmol), diene (0.2 mmol), anhydrous DCE (2 ml) and [Rh(CO)$_2$Cl]$_2$ (0.005 mmol). The flask was degassed and stirred at room temperature. The reaction was monitored by TLC. After the reaction was completed, the reaction mixture was filtered through a small pad of Celite, the filtrate was concentrated under vacuum and the crude mixture was used for the next step without further purification.

The crude mixture from the previous paragraph in xylene (1 ml) was heated at 140° C. for 2 h. The solvent was evaporated and the residue was purified by flash column chromatography.

Characterization Data for Selected Compounds (8a, 8b, 8f, 8i, 10g and 14):

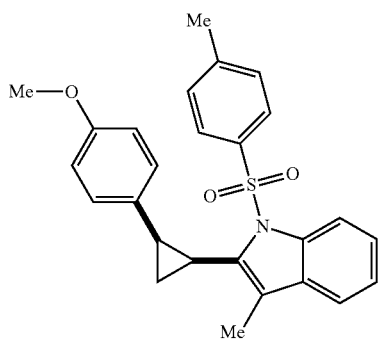

8a: 2-(2-(4-methoxyphenyl)cyclopropyl)-3-methyl-1-tosyl-1H-indole. White solid. 34.5 mg. m.p.=155-156° C. $^1$H NMR (500 MHz, CDCl$_3$, TMS): δ 1.50-1.54 (m, 1H), 1.69-1.73 (m, 1H), 2.08 (s, 3H), 2.28 (s, 3H), 2.48-2.51 (m, 2H), 3.65 (s, 3H), 6.55 (d, J=9.0 Hz, 2H), 6.78 (d, J=9.0 Hz, 2H), 7.05 (d, J=8.0 Hz, 2H), 7.13-7.18 (m, 2H), 7.24-7.26 (m, 1H), 7.40 (d, J=8.0 Hz, 2H), 7.87 (d, J=8.0 Hz, 1H). $^{13}$C NMR (125 MHz, CDCl$_3$): δ 10.3, 15.2, 19.0, 21.7, 23.9, 55.3, 113.4, 115.3, 118.6, 121.1, 123.3, 124.5, 126.5, 128.2, 129.6, 131.2, 131.7, 133.8, 136.4, 136.9, 144.2, 157.8. IR ν 2963, 2343, 1717, 1651, 1520 cm$^{-1}$. HRMS (ESI) for C$_{26}$H$_{25}$NO$_3$S (M+Na), 454.1447 (Calc.), found 454.1442.

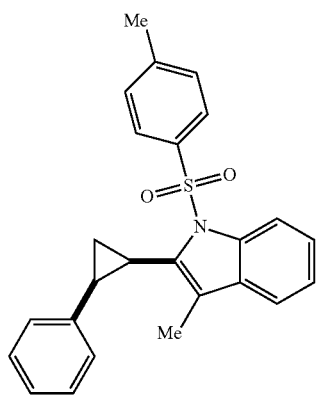

8b: 3-methyl-2-(2-phenylcyclopropyl)-1-tosyl-1H-indole. White solid. 19.2 mg. m.p.=156-157° C. $^1$H NMR (500 MHz, CDCl$_3$, TMS): δ 1.57-1.61 (m, 1H), 1.73-1.78 (m, 1H), 2.07 (s, 3H), 2.27 (s, 3H), 2.52-2.62 (m, 2H), 6.84 (d, J=8.5 Hz, 2H), 6.97-6.70 (m, 3H), 7.04 (d, J=8.5 Hz, 2H), 7.12-7.17 (m, 2H), 7.24-7.26 (m, 1H), 7.39 (d, J=8.5 Hz, 2H), 7.85 (d, J=8.0 Hz, 1H). $^{13}$C NMR (125 MHz, CDCl$_3$): δ 10.3, 15.6, 19.5, 21.7, 24.6, 115.3, 118.6, 121.3, 123.3, 124.5, 125.7, 126.6, 127.2, 127.8, 129.7, 131.6, 133.6, 136.3, 136.8, 139.3, 144.2. IR ν 2955, 2320, 1651, 1522 cm$^{-1}$. HRMS (ESI) for C$_{25}$H$_{23}$NO$_2$S (M+Na), 424.1342 (Calc.), found 424.1338.

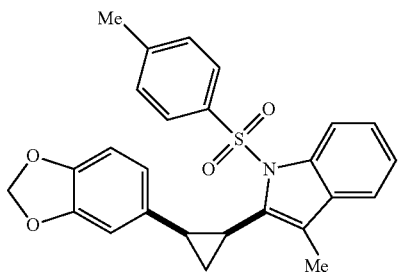

8f

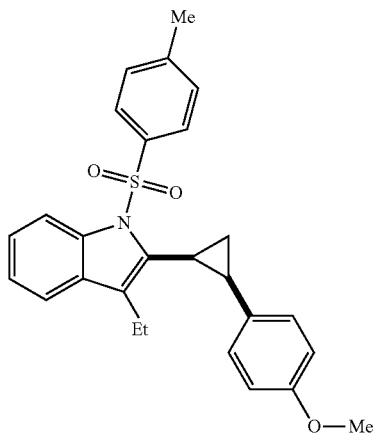

10g

8f: 2-(2-(benzo[d][1,3]dioxol-5-yl)cyclopropyl)-3-methyl-1-tosyl-1H-indole. White solid. 34.7 mg. m.p.=106-107° C. $^1$H NMR (500 MHz, CDCl$_3$, TMS): δ 1.49-1.55 (m, 1H), 1.68-1.73 (m, 1H), 2.14 (s, 3H), 2.28 (s, 3H), 2.45-2.55 (m, 2H), 5.76 (d, J=16.5 Hz, 2H), 6.38 (d, J=8.0 Hz, 2H), 6.47 (d, J=8.0 Hz, 1H), 7.06 (d, J=8.0 Hz, 2H), 7.14-7.19 (m, 2H), 7.27 (d, J=8.5 Hz, 1H), 7.42 (d, J=8.5 Hz, 2H), 7.90 (d, J=8.5 Hz, 1H). $^{13}$C NMR (125 MHz, CDCl$_3$): δ 10.3, 15.1, 19.2, 21.7, 24.3, 100.7, 107.8, 108.0, 115.3, 118.6, 120.5, 121.0, 123.3, 124.5, 126.5, 129.6, 131.6, 133.0, 133.6, 136.4, 136.8, 144.2, 145.7, 147.2. IR ν 2943, 2322, 1712, 1652, 1520 cm$^{-1}$. HRMS (ESI) for C$_{26}$H$_{23}$NO$_4$S (M+Na), 468.1224 (Calc.), found 468.1228.

10g: 3-ethyl-2-(2-(4-methoxyphenyl)cyclopropyl)-1-tosyl-1H-indole. Colorless oil. 54 mg, dr=5:1. $^1$H NMR (500 MHz, CDCl$_3$, TMS) major isomer: δ 7.88 (d, J=9.0 Hz, 1H), 7.37 (d, J=8.5 Hz, 2H), 7.31-7.29 (m, 1H), 7.14-7.08 (m, 2H), 7.02 (d, J=8.0 Hz, 2H), 6.84 (d, J=8.5 Hz, 2H), 6.56 (d, J=9.0 Hz, 2H), 3.64 (s, 3H), 2.73-2.65 (m, 1H), 2.53-2.48 (m 3H), 2.52 (s, 3H), 1.73-1.71 (m, 1H), 1.52-1.48 (m, 1H), 1.10 (t, J=7.5 Hz, 3H). $^{13}$C NMR (125 MHz, CDCl$_3$): δ 157.8, 144.1, 137.2, 136.2, 133.6, 131.2, 131.0, 129.5, 128.4, 126.4, 124.3, 123.3, 118.8, 115.6, 114.1, 113.4, 55.3, 23.8, 21.7, 18.9, 18.1, 15.1, 14.2. IR (CH$_2$Cl$_2$) ν 3663, 2349, 2321, 1711, 1641 cm$^{-1}$. HRMS (ESI) m/z calcd for C$_{27}$H$_{27}$NO$_3$S (M+Na)$^+$ 468.1604 found 468.1605.

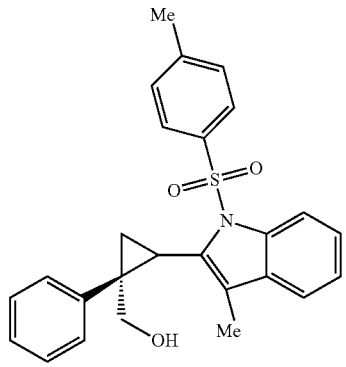

8i

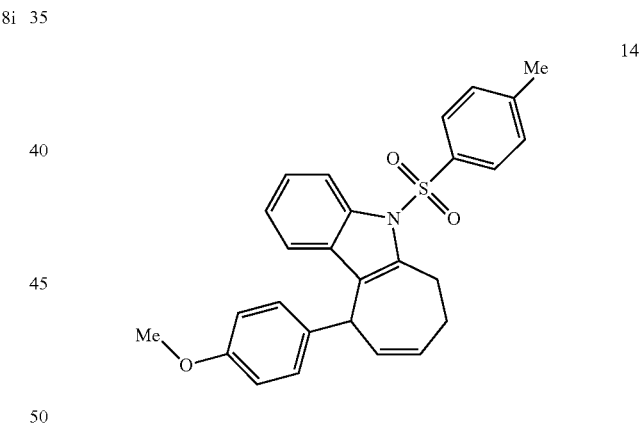

14

8i: (2-(3-methyl-1-tosyl-1H-indol-2-yl)-1-phenylcyclopropyl)methanol. White solid. 22.4 mg. m.p.=57-58° C. $^1$H NMR (400 MHz, CDCl$_3$, TMS): δ 1.53-1.55 (m, 1H), 1.92 (t, J=6.0 Hz, 1H), 2.05 (s, 3H), 2.31 (s, 3H), 2.59-2.65 (m, 2H), 3.96 (s, 2H), 7.00-7.04 (m, 1H), 7.09-7.13 (m, 5H), 7.18 (t, J=8.0 Hz, 2H), 7.41 (d, J=8.0 Hz, 2H), 7.49 (d, J=8.0 Hz, 2H), 7.98 (d, J=8.0 Hz, 1H). $^{13}$C NMR (100 MHz, CDCl$_3$): δ 10.4, 16.9, 21.8, 23.1, 34.4, 71.4, 115.1, 118.6, 119.8, 123.5, 124.7, 126.4, 126.8, 128.1, 129.6, 129.9, 131.9, 133.1, 136.0, 136.6, 138.6, 144.7. IR ν 3365, 2921, 2349, 1717, 1651 cm$^{-1}$. HRMS (ESI) for C$_{26}$H$_{25}$NO$_3$S (M+Na), 454.1447 (Calc.), found 454.1443.

14: (Z)-10-(4-methoxyphenyl)-5-tosyl-5,6,7,10-tetrahydrocyclohepta[b]indole. White solid, 23.2 mg, m.p.=75-76° C. $^1$H NMR (500 MHz, CDCl$_3$, TMS): δ 2.13-2.19 (m, 1H), 2.29-2.38 (m, 4H), 3.25-3.38 (m, 2H), 3.73 (s, 3H), 4.83 (d, J=7.0 Hz, 1H), 5.83-5.88 (m, 1H), 6.03 (dd, J=11.0, 7.0 Hz, 1H), 6.71 (d, J=8.5 Hz, 21), 7.00 (d, J=8.5 Hz, 2H), 7.14-7.18 (m, 3H), 7.20-7.25 (m, 2H), 7.56 (d, J=8.5 Hz, 2H), 8.22 (d, J=8.5 Hz, 1H). $^{13}$C NMR (125 MHz, CDCl$_3$): δ 21.8, 25.5, 26.1, 40.8, 55.4, 113.9, 115.5, 118.6, 122.3, 123.8, 124.3, 126.5, 126.9, 128.5, 130.0, 131.2, 132.2, 135.5, 136.5, 136.7, 138.3, 144.8, 158.1. IR ν 2998, 2349, 1717, 1652, 1520 cm$^{-1}$. HRMS (ESI) for C$_{27}$H$_{25}$NO$_3$S (M+Na), 466.1447 (Calc.), found 466.1441.

Biological Activity of Selected Compounds (8a, 8b, 8f, 8i, 10g and 14):

8a: PCSK9, IC$_{50}$=1.8 μM; IL17, IC$_{50}$=10 μM; IL5, IC$_{50}$>30 μM.

8b: PCSK9, $IC_{50}$=20.96 μM.
8f: PCSK9, $IC_{50}$=9.9 uM; IL17, $IC_{50}$=7.3 uM; IL5, $IC_{50}$>30 uM.
8i: GLP-1, $EC_{50}$=7.3 μM.
10g: PCSK9, $IC_{50}$=0.7 μM.
14: GLP-1, $EC_{50}$=28.4 μM.

REFERENCES CITED

The following documents are incorporated herein by reference.
(1) a) Doyle, M. P. *Chem. Rev.* 1986, 86, 919; b) Padwa, A.; Hombuckle, S. F. *Chem. Rev* 1991, 91, 263; c) Padwa, A.; Weingarten, M. D. *Chem. Rev.* 1996, 96, 223; d) Doyle, M. P.; Forbes, D. C. *Chem. Rev.* 1998, 98, 911; e) Davies, H. M. L.; Beckwith, R. E. J. *Chem. Rev.* 2003, 103, 2861; f) Davies, H. M. L.; Hedley, S. J. *Chem. Soc. Rev.* 2007, 36, 1109; g) Davies, H. M. L.; Manning, J. R. *Nature* 2008, 451, 417; h) de Fremont, P.; Marion, N.; Nolan, S. P. *Coord Chem. Rev.* 2009, 253, 862; i) Davies, H. M. L.; Denton, J. R. *Chem. Soc. Rev.* 2009, 38, 3061; j) Vougioukalakis, G. C.; Grubbs, R. H. *Chem. Rev.* 2010, 110, 1746.
(2) a) Ye, T.; McKervey, M. A. *Chem. Rev.* 1994, 94, 1091; b) Doyle, M. P.; McKervey, M. A.; Ye, T. *Modern Catalytic Methods for Organic Synthesis with Diazo Compounds*; John Wiley & Sons: New York, 1998; c) Zhang, Z.; Wang, J. *Tetrahedron* 2008, 64, 6577.
(3) Werner, H. *J. Organomet. Chem.* 1995, 500, 331.
(4) a) Barluenga, J.; Vicente, R.; Lopez, L. A.; Rubio, E.; Tomas, M.; Alvarez-Rua, C. *J. Am. Chem. Soc.* 2004, 126, 470; b) Barluenga, J.; Vicente, R.; Barrio, P.; Lopez, L. A.; Tomas, M. *J. Am. Chem. Soc.* 2004, 126, 5974; c) Barluenga, J.; Vicente, R.; Lopez, L. A.; Tomas, M. *J. Am. Chem. Soc.* 2006, 128, 7050.
(5) a) Shu, X.-Z.; Huang, S.; Shu, D.; Guzei, I. A.; Tang, W. *Angew. Chem. Int. Ed.* 2011, 50, 8153; b) Shu, X.-Z.; Li, X.; Shu, D.; Huang, S.; Schienebeck, C. M.; Zhou, X.; Robichaux, P. J.; Tang, W. *J. Am. Chem. Soc.* 2012, 134, 5211; c) Shu, X.-Z.; Schienebeck, C. M.; Song, W.; Guzei, I. A.; Tang, W. *Angew. Chem. Int. Ed.* 2013, 52, 13601; d) Xu, X.; Liu, P.; Shu, X.-Z.; Tang, W.; Houk, K. N. *J. Am. Chem. Soc.* 2013, 135, 9271.
(6) Shibata, Y.; Noguchi, K.; Tanaka, K. *J. Am. Chem. Soc.* 2010, 132, 7896.
(7) Shu, X.-Z.; Shu, D.; Schienebeck, C. M.; Tang, W. *Chem. Soc. Rev.* 2012, 41, 7698.
(8) a) Liu, R.; Winston-McPherson, G. N.; Yang, Z.-Y.; Zhou, X.; Song, W.; Guzei, I. A.; Xu, X.; Tang, W. *J. Am. Chem. Soc.* 2013, 135, 8201; b) Li, X.; Song, W.; Tang, W. *J. Am. Chem. Soc.* 2013, 135, 16797.
(9) a) Li, S.-M. *Nat. Prod. Rep.* 2010, 27, 57; b) Ali, N. A. S.; Dar, B. A.; Pradhan, V.; Farooqui, M. *Mini-Rev. Med Chem.* 2013, 13, 1792; c) Kaushik, N. K.; Kaushik, N.; Attri, P.; Kumar, N.; Kim, C. H.; Verma, A. K.; Choi, E. H. *Molecules* 2013, 18, 6620.
(10) a) Barluenga, J.; Rodriguez, F.; Fananas, F. J. *Chem. Asian J.* 2009, 4, 1036; b) Taber, D. F.; Tirunahari, P. K. *Tetrahedron* 2011, 67, 7195; c) Vicente, R. *Org. Biomol. Chem.* 2011, 9, 6469; d) Platon, M.; Amardeil, R.; Djakovitch, L.; Hierso, J.-C. *Chem. Soc. Rev.* 2012, 41, 3929.
(11) a) Kothandaraman, P.; Rao, W.; Foo, S. J.; Chan, P. W. H. *Angew. Chem. Int. Ed.* 2010, 49, 4619; b) Kothandaraman, P.; Mothe, S. R.; Toh, S. S. M.; Chan, P. W. H. *J. Org. Chem.* 2011, 76, 7633; c) Susanti, D.; Koh, F.; Kusuma, J. A.; Kothandaraman, P.; Chan, P. W. H. *J. Org. Chem.* 2012, 77, 7166.
(12) Li, H.; Li, X.; Wang, H.-Y.; Winston-McPherson, G. N.; Geng, H.-m. J.; Guzei, I. A.; Tang, W. *Chem. Commun.* 2014, 50, 12293.
(13) a) Holton, T. L.; Shechter, H. *J. Org. Chem.* 1995, 60, 4725; b) McGuiness, M.; Shechter, H. *Tetrahedron Lett.* 2002, 43, 8425; c) Javed, M. I.; Brewer, M. *Org. Lett.* 2007, 9, 1789; d) Moebius, D. C.; Kingsbury, J. S. *J. Am. Chem. Soc.* 2009, 131, 878.
(14) a) Lebel, H.; Marcoux, J.-F.; Molinaro, C.; Charette, A. B. *Chem. Rev.* 2003, 103, 977; b) Kim, H. Y.; Walsh, P. J. *Acc. Chem. Res.* 2012, 45, 1533; c) Bartoli, G.; Bencivenni, G.; Dalpozzo, R. *Synthesis* 2014, 46, 979.
(15) a) Reissig, H. U.; Zimmer, R. *Chem. Rev.* 2003, 103, 1151; b) Nakamura, M.; Isobe, H.; Nakamura, E. *Chem. Rev.* 2003, 103, 1295; c) Rubin, M.; Rubina, M.; Gevorgyan, V. *Chem. Rev.* 2007, 107, 3117; d) Chen, D. Y. K.; Pouwer, R. H.; Richard, J.-A. *Chem. Soc. Rev.* 2012, 41, 4631; e) Tang, P.; Qin, Y. *Synthesis* 2012, 44, 2969.
(16) a) Han, X.; Li, H.; Hughes, R. P.; Wu, J. *Angew. Chem. Int. Ed.* 2012, 51, 10390; b) Shu, D.; Song, W.; Li, X.; Tang, W. *Angew. Chem. Int. Ed,* 2013, 52, 3237.
(17) a) Shafiee, A.; Ahond, A.; Bui, A. M.; Langlois, Y.; Riche, C.; Potier, P. *Tetrahedron Lett.* 1976, 921; b) Andriantsiferana, M.; Bessełievre, R.; Riche, C.; Husson, H. P. *Tetrahedron Lett.* 1977, 2587; c) Carroll, A. R.; Hyde, E.; Smith, J.; Quinn, R. J.; Guymer, G.; Forster, P. I. *J. Org. Chem.* 2005, 70, 1096; d) Taniguchi, T.; Martin, C. L.; Monde, K.; Nakanishi, K.; Berova, N.; Overman, L. E. *J. Nat. Prod* 2009, 72, 430.
(18) a) Napper, A. D.; Hixon, J.; McDonagh, T.; Keavey, K.; Pons, J. F.; Barker, J.; Yau, W. T.; Amouzegh, P.; Flegg, A.; Hamelin, E.; Thomas, R. J.; Kates, M.; Jones, S.; Navia, M. A.; Saunders, J.; DiStefano, P. S.; Curtis, R. *J. Med. Chem.* 2005, 48, 8045; b) Barf, T.; Lehmann, F.; Hammer, K.; Haile, S.; Axen, E.; Medina, C.; Uppenberg, J.; Svensson, S.; Rondahl, L.; Lundbaeck, T. *Bioorg. Med. Chem. Lett.* 2009, 19, 1745; c) Yamuna, E.; Kumar, R. A.; Zeller, M.; Prasad, K. J. R. *Eur J. Med Chem.* 2012, 47, 228.
(19) a) Del Zotto, A.; Baratta, W.; Verardo, G.; Rigo, P. *Eur. J. Org. Chem.* 2000, 2795; b) Hodgson, D. M.; Angrish, D. *Chem. Eur. J.* 2007, 13, 3470; c) Bray, C. V.-L.; Derien, S.; Dixneuf, P. H. *Angew. Chem. Int. Ed.* 2009, 48, 1439.
(20) Johansson, M. J.; Gorin, D. J.; Staben, S. T.; Toste, F. D. *J. Am. Chem. Soc.* 2005, 127, 18002.

What is claimed is:
1. A method of making indoles, the method comprising: contacting a reactant of formula I:

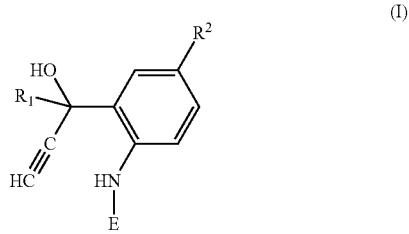

wherein E is a protecting group, —$SO_2$-Aryl, or —$SO_2$-substituted-Aryl; and
$R^1$ and $R^2$ are independently selected from the group consisting of hydrogen, halo, $C_1$-$C_{12}$-alkyl, and aryl;
with a rhodium(I)-containing catalyst, in the presence or absence of an alkene-containing co-reactant, for a time and at a temperature to yield a product mixture comprising a compound selected from the group consisting of formula (II), (III), and (IV):

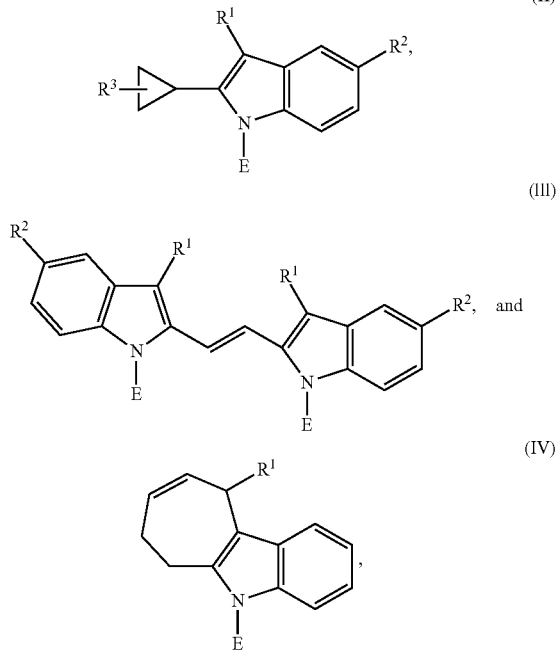

wherein $R^1$, $R^2$, and E are as defined previously, and $R^3$ is hydrogen in the absence of the alkene-containing co-reactant, and $R^3$ is a substituent corresponding to the alkene-containing co-reactant in the presence of the alkene-containing co-reactant.

2. The method of claim 1, which yields a product mixture comprising a compound of formula (II).

3. The method of claim 1, which yields a product mixture comprising a compound of formula (III).

4. The method of claim 1, which yields a product mixture comprising a compound of formula (IV).

5. The method of claim 1, conducted in the absence of the alpha-alkene-containing co-reactant.

6. The method of claim 1, wherein the alkene-containing co-reactant is present and is selected from the group consisting of:

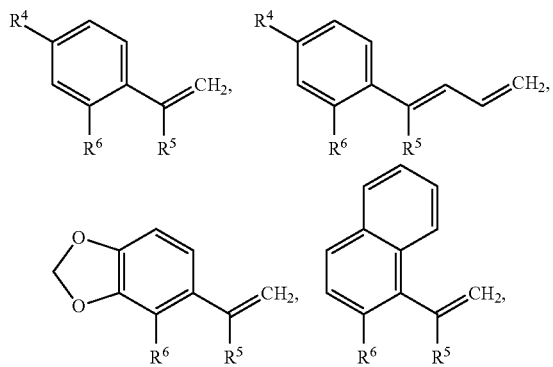

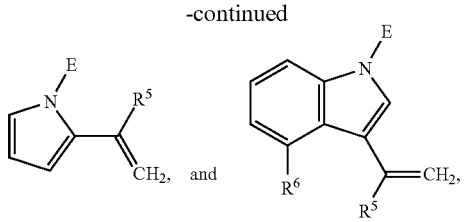

wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; and E is a protecting group.

7. The method of claim 1, wherein the rhodium(I)-containing catalyst comprises $[Rh(CO)_2Cl]_2$.

8. The method of claim 7, which yields a product mixture comprising a compound of formula (II).

9. The method of claim 7, which yields a product mixture comprising a compound of formula (III).

10. The method of claim 7, which yields a product mixture comprising a compound of formula (IV).

11. The method of claim 7, conducted in the absence of the alpha-alkene-containing co-reactant.

12. The method of claim 7, wherein the alkene-containing co-reactant is present and is selected from the group consisting of:

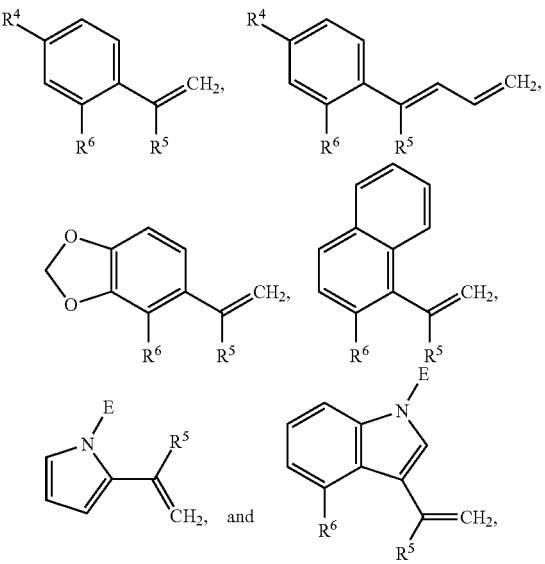

wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; and E is a protecting group.

13. The method of claim 1, wherein the reactant of formula I is contacted with the catalyst in the presence of carbon monoxide.

14. The method of claim 13, which yields a product mixture comprising a compound of formula (II).

15. The method of claim 13, which yields a product mixture comprising a compound of formula (III).

16. The method of claim 13, which yields a product mixture comprising a compound of formula (IV).

17. The method of claim 13, conducted in the absence of the alpha-alkene-containing co-reactant.

18. The method of claim 13, wherein the alkene-containing co-reactant is present and is selected from the group consisting of:

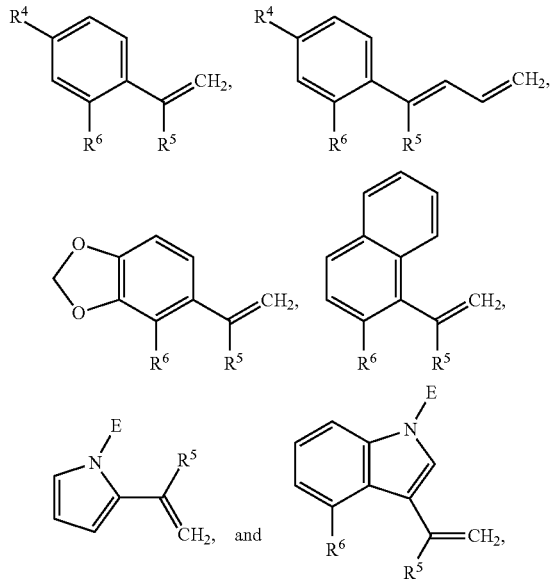

wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; and E is a protecting group.

19. A method of treating hyperglycemic, hyperlipidemic, or autoimmune disorders in mammals, wherein the autoimmune disorders are selected from the group consisting of arthritis, multiple sclerosis, psoriasis, and inflammatory bowel disease, the method comprising administering to a mammal an anti-hyperglycemic-effective, anti-hyperlipidemic-effective, or anti-autoimmune-effective amount of one or more compounds selected from the group consisting of:

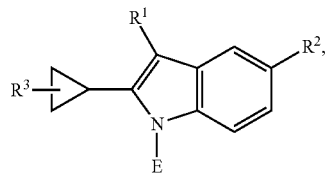

wherein $R^1$ and $R^2$ are independently selected from the group consisting of hydrogen, halo, $C_1$-$C_{12}$-alkyl, and aryl; and $R^3$ is selected from the group consisting of:

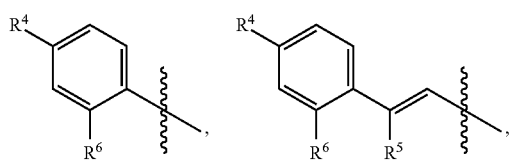

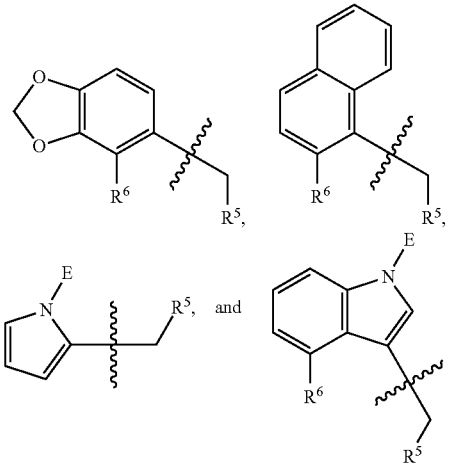

wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; E is a protecting group or a hydrogen atom;

or a pharmaceutically suitable salt thereof.

20. A pharmaceutical composition for treating hyperglycemic, hyperlipidemic, or autoimmune disorders in mammals, wherein the autoimmune disorders are selected from the group consisting of arthritis, multiple sclerosis, psoriasis, and inflammatory bowel disease, the composition comprising an anti-hyperglycemic-effective, anti-hyperlipidemic-effective, or anti-autoimmune-effective amount of one or more of the compounds selected from the group consisting of:

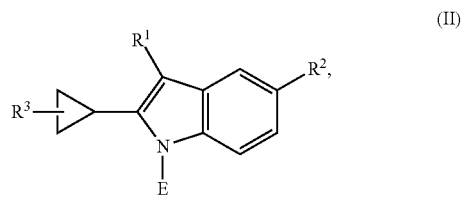

wherein $R^1$ and $R^2$ are independently selected from the group consisting of hydrogen, halo, $C_1$-$C_{12}$-alkyl, and aryl; and $R^3$ is selected from the group consisting of:

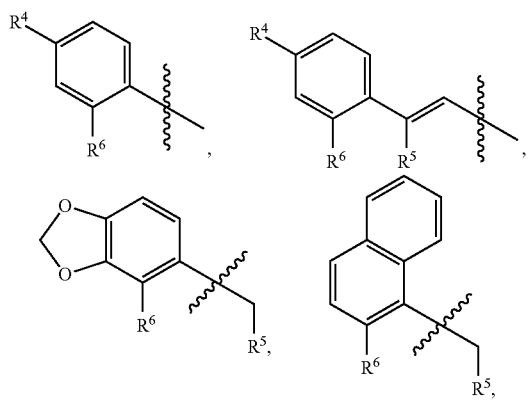

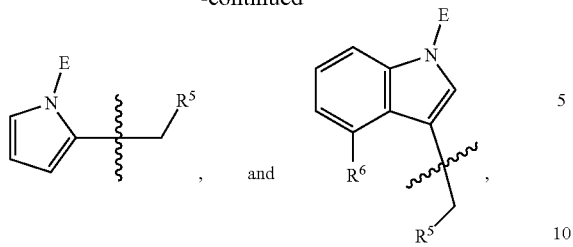
wherein $R^4$, $R^5$, and $R^6$ are each independently selected from the group consisting of hydrogen, $C_1$-$C_{12}$-alkyl, $C_1$-$C_{12}$-alkyloxy, $C_1$-$C_{12}$-haloalkyl, and $C_1$-$C_{12}$-hydroxyalkyl; E is a protecting group or a hydrogen atom;
or a pharmaceutically suitable salt thereof;
in combination with a pharmaceutically suitable carrier.
* * * * *